(12) United States Patent
Nomura et al.

(10) Patent No.: US 8,071,591 B2
(45) Date of Patent: Dec. 6, 2011

(54) 7-CYCLOALKYLAMINOQUINOLONES AS GSK-3 INHIBITORS

(75) Inventors: Masahiro Nomura, Shimotsuga-gun (JP); Kyoko Okada, Shimotsuga-gun (JP); Taro Sato, Shimotsuga-gun (JP); Yasushi Kohno, Shimotsuga-gun (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 12/721,454

(22) Filed: Mar. 10, 2010

(65) Prior Publication Data
US 2010/0234367 A1  Sep. 16, 2010

Related U.S. Application Data

(60) Provisional application No. 61/159,409, filed on Mar. 11, 2009.

(51) Int. Cl.
*C07D 498/06* (2006.01)
*A61K 31/5383* (2006.01)

(52) U.S. Cl. .................................. 514/230.2; 544/101

(58) Field of Classification Search .................. 544/101; 514/230.2
See application file for complete search history.

(56) References Cited

U.S. PATENT DOCUMENTS

| | | |
|---|---|---|
| 3,536,809 A | 10/1970 | Zaffaroni et al. |
| 3,598,123 A | 8/1971 | Zaffaroni et al. |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,044,126 A | 8/1977 | Cook et al. |
| 4,364,923 A | 12/1982 | Cook et al. |
| 4,414,209 A | 11/1983 | Cook et al. |
| 4,762,831 A | 8/1988 | Grohe et al. |
| 4,847,375 A | 7/1989 | Grohe et al. |
| 4,990,508 A | 2/1991 | Narita et al. |
| 5,033,252 A | 7/1991 | Carter |
| 5,052,558 A | 10/1991 | Carter |
| 5,059,595 A | 10/1991 | Le Grazie |
| 5,073,543 A | 12/1991 | Marshall et al. |
| 5,120,548 A | 6/1992 | McClelland et al. |
| 5,153,203 A | 10/1992 | Yatsunami et al. |
| 5,190,923 A | 3/1993 | Vincent et al. |
| 5,323,907 A | 6/1994 | Kalvelage |
| 5,354,556 A | 10/1994 | Sparks et al. |
| 5,387,748 A | 2/1995 | Demuth, Jr. et al. |
| 5,430,152 A | 7/1995 | Saukaitis et al. |
| 5,591,767 A | 1/1997 | Mohr et al. |
| 5,612,059 A | 3/1997 | Cardinal et al. |
| 5,639,476 A | 6/1997 | Oshlack et al. |
| 5,639,480 A | 6/1997 | Bodmer et al. |
| 5,674,533 A | 10/1997 | Santus et al. |
| 5,709,874 A | 1/1998 | Hanson et al. |
| 5,733,566 A | 3/1998 | Lewis |
| 5,739,108 A | 4/1998 | Mitchell |
| 5,759,542 A | 6/1998 | Gurewich |
| 5,798,119 A | 8/1998 | Herbig et al. |
| 5,840,674 A | 11/1998 | Yatvin et al. |
| 5,891,474 A | 4/1999 | Busetti et al. |
| 5,900,252 A | 5/1999 | Calanchi et al. |
| 5,922,356 A | 7/1999 | Koseki et al. |
| 5,972,366 A | 10/1999 | Haynes et al. |
| 5,972,891 A | 10/1999 | Kamei et al. |
| 5,980,945 A | 11/1999 | Ruiz |
| 5,985,307 A | 11/1999 | Hanson et al. |
| 5,993,855 A | 11/1999 | Yoshimoto et al. |
| 6,004,534 A | 12/1999 | Langer et al. |
| 6,039,975 A | 3/2000 | Shah et al. |
| 6,045,830 A | 4/2000 | Igari et al. |
| 6,048,736 A | 4/2000 | Kosak |
| 6,060,082 A | 5/2000 | Chen et al. |
| 6,071,495 A | 6/2000 | Unger et al. |
| 6,087,324 A | 7/2000 | Igari et al. |
| 6,113,943 A | 9/2000 | Okada et al. |
| 6,120,751 A | 9/2000 | Unger |
| 6,131,570 A | 10/2000 | Schuster et al. |
| 6,139,865 A | 10/2000 | Friend et al. |
| 6,197,350 B1 | 3/2001 | Yamagata et al. |
| 6,221,633 B1 | 4/2001 | Ertl et al. |
| 6,221,897 B1 | 4/2001 | Frick et al. |

(Continued)

FOREIGN PATENT DOCUMENTS

CN   1181381   11/1997

(Continued)

OTHER PUBLICATIONS

Asakawa, et al., Horm. Metab.Re. 33(9):554-58, 2001.
Atarashi, et al., Chem. Pharm. Bull. 35(5):1896-902, 1987.
Atarashi, et al., J. Heterocyclic Chem., 28, 329, 1991.
Buchwald, et al., Surgery 88(4):507-16, 1980.
Calas, et al., Eur. J. Med. Chem. 26:279-290, 1991.
Coghlan, et al., Chemistry & Biology 7(10):793-03, 2000.
Doyle, et al., J. Org. Chem. 42(14): 2426-31, 1977.
Egawa, et al., Chem. Pharm. Bull., 34, 4098 1986.
Fujita, et al., Chem. Pharm. Bull. 44(5):987-90, 1996.
Golub, et al., J. Med. Chem 49: 6443, 2006.

(Continued)

Primary Examiner — Kahsay T Habte
(74) Attorney, Agent, or Firm — Jones Day

(57) ABSTRACT

Provided herein are aminoquinolones of formula I and compositions containing the compounds, wherein formula I is

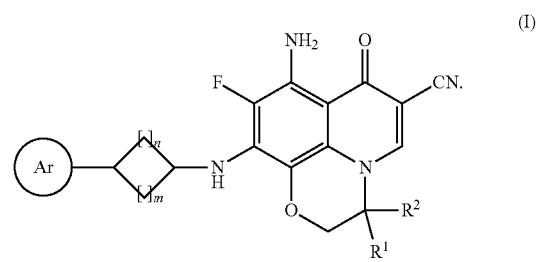

(I)

The compounds and compositions provided herein are useful in the amelioration or treatment of GSK-3 inhibitors mediated diseases.

10 Claims, No Drawings

U.S. PATENT DOCUMENTS

| | | |
|---|---|---|
| 6,245,744 B1 | 6/2001 | Frick et al. |
| 6,248,363 B1 | 6/2001 | Patel et al. |
| 6,253,872 B1 | 7/2001 | Neumann |
| 6,264,970 B1 | 7/2001 | Hata et al. |
| 6,267,981 B1 | 7/2001 | Okamoto et al. |
| 6,271,359 B1 | 8/2001 | Norris et al. |
| 6,274,552 B1 | 8/2001 | Tamarkin et al. |
| 6,316,652 B1 | 11/2001 | Steliou |
| 6,342,512 B1 | 1/2002 | Kirsch et al. |
| 6,350,458 B1 | 2/2002 | Modi |
| 6,376,461 B1 | 4/2002 | Igari et al. |
| 6,419,961 B1 | 7/2002 | Igari et al. |
| 6,589,548 B1 | 7/2003 | Oh et al. |
| 6,613,358 B2 | 9/2003 | Randolph et al. |
| 6,699,500 B2 | 3/2004 | Okada et al. |
| 6,740,634 B1 | 5/2004 | Saikawa et al. |
| 6,825,353 B2 | 11/2004 | Saito et al. |
| 6,967,205 B1 | 11/2005 | Abdul-Rahman |
| 2004/0019932 A1 | 1/2004 | Allen et al. |
| 2004/0132764 A1 | 7/2004 | Locher |
| 2005/0054663 A1 | 3/2005 | Bennett et al. |
| 2005/0182085 A1 | 8/2005 | Defossa et al. |
| 2007/0254866 A1 | 11/2007 | Cociorva et al. |

FOREIGN PATENT DOCUMENTS

| | | |
|---|---|---|
| CN | 1491944 A | 4/2004 |
| EP | 0 265 230 A1 | 4/1988 |
| EP | 0 390 215 A2 | 10/1990 |
| EP | 0 945 435 A1 | 9/1999 |
| EP | 1 486 488 A1 | 12/2004 |
| EP | 1 650 192 A1 | 4/2006 |
| ES | 206819 | 5/1992 |
| JP | S59-1489 | 1/1984 |
| JP | 62198685 | 2/1986 |
| JP | S62-53987 | 5/1986 |
| JP | S62-167769 | 1/1987 |
| JP | S62-252772 | 4/1987 |
| JP | S63-264439 | 1/1988 |
| JP | S63-132891 | 6/1988 |
| JP | 03133983 | 10/1989 |
| JP | H1-268679 | 10/1989 |
| JP | H5-25162 | 2/1993 |
| WO | WO 97/26265 | 7/1997 |
| WO | WO 97/41097 | 11/1997 |
| WO | WO 98/08871 | 3/1998 |
| WO | WO 99/15525 | 4/1999 |
| WO | WO 99/65897 | 12/1999 |
| WO | WO 00/38675 | 7/2000 |
| WO | WO 00/40569 | 7/2000 |
| WO | WO 00/63208 | 10/2000 |
| WO | WO 00/66585 | 11/2000 |
| WO | WO 00/71549 A1 | 11/2000 |
| WO | WO 00/78312 A1 | 12/2000 |
| WO | WO 01/09111 A1 | 2/2001 |
| WO | WO 01/83451 A1 | 11/2001 |
| WO | WO 01/85695 A1 | 11/2001 |
| WO | WO 02/09758 A2 | 2/2002 |
| WO | WO 02/17918 | 3/2002 |
| WO | WO 0204462 | 6/2002 |
| WO | WO 02/092571 A1 | 11/2002 |
| WO | WO 02/004462 A1 | 8/2003 |
| WO | WO 2004/089930 | 10/2004 |
| WO | WO 2004/096221 A1 | 11/2004 |
| WO | WO 2005/007111 A2 | 1/2005 |
| WO | WO 2009/035634 | 3/2009 |
| WO | WO 2009/035684 | 3/2009 |

OTHER PUBLICATIONS

Guo, II., et al., Inst. Med. Biol. Tech. Chin, Abstract, 2004.
Haq, et al., J. Cell. Biol. 151(1):117-29, 2000.
Havlicek, et. al., J. Med. Chem. 40:408-12, 1997.
Kaiho, et al., J. Med. Chem., 32, 351, 1989.
Kawatsura, et al., Tetrahedron, 63, 4172, 2007.
Kiely, et al., J. Heterocyclic Chem. 26(6):1675-81, 1989.
Kiely, et al., J. Med. Chem. 31:2004-2008, 1988.
Kim, et al., Curr. Opin. Genetics & Dev. 10:508-14, 2000.
Kobayashi, et al., Org. Lett., 7, 1319, 2005.
Kobayashi, et al., Org. Lett., 7, 183, 2005.
Koga, et al., J. Med. Chem., 23, 1358, 1980.
Kondo, et al., J. Med. Chem. 31:221-25, 1988.
Langer, Sciencc 249(4976):1527-33, 1990.
Lee, et al., Drugs of the Future 26(9):873-81, 2001.
Mitscher, et al., J. Med. Chem., 30, 2283, 1987.
Miyamoto, et al., J. Med. Chem. 33:1645-56, 1990.
Mullen, et al., J. Med. Chem. 31, 1694, 1988.
Remuzon, et al., J. Med. Chem.,, 34, 29, 1991.
Santus and Baker, J. Controlled Release, 35, 1-21, 1995.
Saloutin, et al., J. Fluoerine Chem. 65:37-41, 1993.
Salvador, et al., Expert Opinion on Pharmacotherapy 2(10):1615-22, 2001.
Saudek, et al., N. Engl. J. Med. 321(9):574-79, 1989.
Sbardella, et al., IL Farmaco 59:463-71, 2004.
Sefton, CRC Crit. Rev. Biomed. Eng. 14(3):201-40, 1987.
Shibamori, et al., Chem. Pharm. Bull. 38(9):2390-96, 1990.
Singh, R., et al., Eur. J. Med. Chem., 33:697-03, 1998.
Wentland, et al., J. Med. Chem. 31:1694-1697, 1988.
Wentland, et al, Bioorg. Med. Chem Lett. 3 (8) 1711-1716, 1993.
Verma, et al., Drug Development and Industrial Pharmacy, 26, 695-708, 2000.
Verma, et al., J. Controlled Release, 79, 7-27, 2002.
U.S.P.T.O. non-Final Office Action dated Oct. 16, 2008 for U.S. Appl. No. 11/718,000, filed Mar. 13, 2007.
U.S.P.T.O. Final Office Action dated May 14, 2009 for U.S. Appl. No. 11/718,000, filed Mar. 13, 2007.
U.S.P.T.O. non-Final Office Action dated Dec. 9, 2009 for U.S. Appl. No. 11/718,000, filed Mar. 13, 2007.
U.S.P.T.O. non-Final Office Action dated Jul. 7, 2010 for U.S. Appl. No. 11/718,000, filed Mar. 13, 2007.
U.S.P.T.O. Notice of Allowance Jan. 14, 2011 for U.S. Appl. No. 11/718,000, filed Mar. 13, 2007.
Toda et al., *Chem. Pharma. Bull*, 42(12): 2569-2574.
English abstract of CN 1491944A to Guo, H., et al., 2004.

7-CYCLOALKYLAMINOQUINOLONES AS GSK-3 INHIBITORS

RELATED APPLICATIONS

This application claims priority to U.S. provisional application No. 61/159,409, filed Mar. 11, 2009. The disclosure of the above referenced application is incorporated by reference herein in its entirety.

FIELD

Compounds, compositions and methods for treating GSK-3 mediated diseases are provided. The compounds provided herein are aminoquinolones that are GSK-3 inhibitors.

BACKGROUND

Glycogen synthase kinase-3 (GSK-3) is a serine/threonine protein kinase having α and β isoforms that are each encoded by distinct genes [Coghlan et al., *Chemistry & Biology*, 7, 793-803 (2000); and Kim and Kimmel, *Curr. Opinion Genetics Dev.*, 10, 508-514 (2000)]. GSK-3 has been implicated in various diseases including diabetes, Alzheimer's disease, CNS disorders such as manic depressive disorder and neurodegenerative diseases, and cardiomyocete hypertrophy [see, e.g., WO 99/65897; WO 00/38675; and Haq et al., *J. Cell Biol.* (2000) 151, 117]. These diseases may be caused by, or may result in, the abnormal operation of certain cell signaling pathways in which GSK-3 plays a role.

GSK-3 has been found to phosphorylate and modulate the activity of a number of regulatory proteins. These include glycogen synthase, which is the rate-limiting enzyme required for glycogen synthesis, the microtubule-associated protein Tau, the gene transcription factor β-catenin, the translation initiation factor e1F-2B, as well as ATP citrate lyase, axin, heat shock factor-1, c-Jun, c-myc, c-myb, CREB, and CEPB α. These diverse targets implicate GSK-3 in many aspects of cellular metabolism, proliferation, differentiation and development.

Small molecule inhibitors of GSK-3 have recently been reported in, for example, WO 99/65897 (Chiron) and WO 00/38675 (SmithKline Beecham), however, there is a continued need to find more effective therapeutic agents to treat GSK-3 mediated diseases.

SUMMARY

Provided herein are compounds represented by Formula (I):

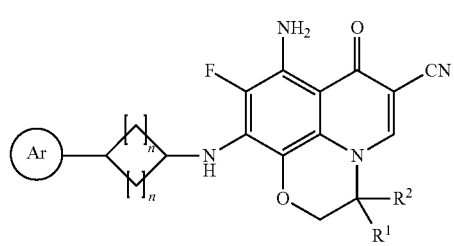

or a pharmaceutically acceptable salt thereof, wherein
$R^1$ is lower alkyl;
$R^2$ is hydrogen or lower alkyl;
m is 1, 2 or 3;
n is 1 or 2;
Ar is aryl or heteroaryl which is optionally substituted with one to three substituents, each independently selected from Q groups;
wherein Q is halo, hydroxy, cyano, nitro, oxo, thioxo, hydroxycarbonyl, alkyl, haloalkyl, alkenyl, alkynyl, cycloalkyl, heterocyclyl, aryl, heteroaryl, aralkyl, heteroaralkyl, alkoxy, haloalkoxy, cycloalkoxy, heterocyclyloxy, aryloxy, heteroaryloxy, aralkyloxy, heretoaralkyloxy, alkylcarbonyl, arylcarbonyl, heteroarylcarbonyl, alkoxycarbonyl, aryloxycarbonyl, aralkyloxycarbonyl, unsubstituted or substituted aminocarbonyl, alkylcarbonyloxy, arylcarbonyloxy, aralkylcarbonyloxy, alkoxycarbonyloxy, aryloxycarbonyloxy, aralkyloxycarbonyloxy, unsubstituted or substituted aminocarbonyloxy, unsubstituted or substituted amino, alkylthio, cycloalkylthio, arylthio, heteroarylthio, aralkylthio, heteroaralkylthio, alkylsulfinyl, cycloalkylsulfinyl, arylsulfinyl, heteroarylsulfinyl, aralkylsulfinyl, heteroaralkylsulfinyl, alkylsulfonyl, cycloalkylsulfonyl, arylsulfonyl, heteroarylsulfonyl, aralkylsulfonyl, heteroaralkylsulfonyl, alkoxysulfonyl, aryloxysulfonyl, unsubstituted or substituted aminosulfonyl, or hydroxysulfonyl.

Also provided herein are pharmaceutical compositions containing a compound of Formula (I) and a pharmaceutically acceptable carrier.

Further provided herein are methods for treating, preventing, or ameliorating one or more symptoms of GSK-3 mediated diseases by administering the compounds and compositions provided herein.

DETAILED DESCRIPTION OF EMBODIMENTS

A. Definitions

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

As used herein, the nomenclature alkyl, alkoxy, carbonyl, etc. is used as is generally understood by those of skill in this art.

As used herein, alkyl carbon chains, if not specified, contain from 1 to 20 carbons, 1 to 16 carbons or 1 to 6 carbons and are straight or branched. In certain embodiments, alkyl carbon chains contain from 1 to 6 carbons. Exemplary alkyl groups herein include, but are not limited to, methyl, ethyl, propyl, isopropyl, isobutyl, n-butyl, sec-butyl, tert-butyl, isopentyl, neopentyl, tert-pentyl, isohexyl. As used herein, lower alkyl refers to carbon chains having from about 1 carbons up to about 6 carbons.

As used herein, alkenyl carbon chains, if not specified, contain from 2 to 20 carbons, 2 to 16 carbons or 2 to 6 carbons and are straight or branched. In certain embodiments, alkenyl carbon chains contain from 2 to 6 carbons. Alkenyl carbon chains of from 2 to 20 carbons, in certain embodiments, contain 1 to 8 double bonds, and the alkenyl carbon chains of 2 to 16 carbons, in certain embodiments, contain 1 to 5 double bonds. The alkenyl carbon chains of 2 to 6 carbons, in certain embodiments, contain 1 to 2 double bonds. Exemplary alkenyl groups herein include, but are not limited to, vinyl, 1-propenyl, 2-propenyl, isopropenyl, 1-butenyl, 2-butenyl, 3-butenyl, 1,3-butadienyl. As used herein, lower alkenyl refer to carbon chains having from about 2 carbons up to about 6 carbons.

As used herein, alkynyl carbon chains, if not specified, contain from 2 to 20 carbons, 2 to 16 carbons or 2 to 6 carbons and are straight or branched. In certain embodiments, alkynyl carbon chains contain from 2 to 6 carbons. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Alkynyl carbon chains of from 2 to 6 carbons, in certain embodiments, contain 1 to 2 triple bonds. Exemplary alkynyl groups herein include, but are not limited to, ethynyl, 1-propynyl and 2-propynyl. As used herein, lower alkynyl refer to carbon chains having from about 2 carbons up to about 6 carbons.

As used herein, "alkoxy" contain from 1 to 20 carbons, 1 to 16 carbons or 1 to 6 carbons and are straight or branched. In certain embodiments, alkoxy carbon chains contain from 1 to 6 carbons. Exemplary alkoxy groups herein include, but are not limited to, methoxy, ethoxy, propoxy, isopropoxy, isobutoxy, n-butoxy, sec-butoxy, tert-butoxy, isopentoxy, neopentoxy, tert-pentoxy and isohexyloxy.

As used herein, "aralkyl" refers to an alkyl group in which one of the hydrogen atoms of the alkyl is replaced by an aryl.

As used herein, "halo", "halogen" or "halide" refers to F, Cl, Br or I.

As used herein, "aryl" refers to aromatic monocyclic or multicyclic groups containing from 6 to 19 carbon atoms. Aryl groups include, but are not limited to groups such as fluorenyl, substituted fluorenyl, phenyl, substituted phenyl, naphthyl and substituted naphthyl.

As used herein, "cycloalkyl" refers to a saturated mono- or multicyclic ring system, in certain embodiments of 3 to 10 carbon atoms, in other embodiments of 3 to 6 carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 carbon atoms, with cycloalkenyl groups, in further embodiments, containing 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, aminocarbonyl, alkoxycarbonyl, guanidino, or the nitrogen may be quaternized to form an ammonium group where the substituents are selected as above.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, N-methylpyrrolyl, quinolinyl and isoquinolinyl.

As used herein, "fused heterocyclylaryl" refers to aryl which was fused with a heterocyclyl group. In one embodiment, fused heterocyclylaryls are those wherein heterocyclyl contains about 5 to about 6 ring atoms and the aryl thereof is phenyl. A fused heterocyclylaryl may be bonded through any atom of the ring system. Representative fused heterocycylylaryl groups include 1,3-benzodioxolan-4-yl, 1,3-benzodioxolan-5-yl, 1,3-benzodioxolan-6-yl, 1,3-benzodioxolan-7-yl, 4-indolinyl, 5-indolinyl, 6-indolinyl and 7-indolinyl.

As used herein, "fused arylheterocyclyl" refers to fused heterocyclyl which was fused to an aryl group. In one embodiment, fused arylheterocylyls are those wherein the aryl thereof is phenyl and the heterocyclyl contains about 5 to about 6 ring atoms. A fused arylheterocyclyl may be bonded through any atom of the ring system. Representative fused arylheterocyclyl groups include 1-indolinyl, 2-indolinyl, 3-indolinyl, 1,2,3,4-tetrahydroqunolin-1-yl, 1,2,3,4-tetrahydroqunolin-2-yl, 1,2,3,4-tetrahydroqunolin-3-yl and 1,2,3,4-tetrahydroqunolin-4-yl.

As used herein, "haloalkyl" refers to an alkyl group in which one or more of the hydrogen atoms are replaced by halogen. "Lower haloalkyl" refers to a lower alkyl group in which one or more of the hydrogen atoms are replaced by halogen. Such groups include, but are not limited to, chloromethyl, trifluoromethyl and 1-chloro-2-fluoroethyl.

As used herein, "heteroaralkyl" refers to an alkyl group in which one of the hydrogen atoms are replaced by heteroaryl.

As used herein, "haloalkoxy" refers to RO— in which R is a haloalkyl group.

As used herein, "cycloalkoxy" refers to RO— in which R is a cycloalkyl group.

As used herein, "aryloxy" refers to RO— in which R is an aryl.

As used herein, "heteroaryloxy" refers to RO— in which R is a heteroaryl.

As used herein, "heterocyclyloxy" refers to RO— in which R is a heterocyclyl.

As used herein, "aralkyloxy" refers to RO— in which R is an aralkyl.

As used herein, "heteroaralkyloxy" refers to RO— in which R is a heteroaralkyl.

As used herein, "alkylcarbonyl" refers to RCO— in which R is an alkyl group.

As used herein, "arylcarbonyl" refers to RCO— in which R is an aryl.

As used herein, "heteroarylcarbonyl" refers to RCO— in which R is a heteroaryl.

As used herein, "alkoxycarbonyl" refers to RCO— in which R is an alkoxy group.

As used herein, "aryloxycarbonyl" refers to RCO— in which R is an aryl.

As used herein, "aralkyloxycarbonyl" refers to RCO— in which R is an aralkyl.

As used herein, "unsubstituted or substituted aminocarbonyl" refers to —C(O)NR'R in which R' and R are independently hydrogen, alkyl aryl, heteroaryl, aralkyl or heteroaralkyl.

As used herein, "alkylcarbonyloxy" refers to —OC(O)R in which R is alkyl.

As used herein, "arylcarbonyloxy" refers to —OC(O)R in which R is aryl.

As used herein, "aralkylcarbonyloxy" refers to —OC(O)R in which R is aralkyl.

As used herein, "alkoxycarbonyloxy" refers to —OC(O)OR in which R is alkyl.

As used herein, "aryloxycarbonyloxy" refers to —OC(O)OR in which R is aryl.

As used herein, "aralkyloxycarbonyloxy" refers to —OC(O)OR in which R is aralkyl.

As used herein, "unsubstituted or substituted aminocarbonyloxy" refers to —OC(O)NR'R in which R' and R are independently hydrogen, alkyl aryl, heteroaryl, aralkyl or heteroaralkyl.

As used herein, "unsubstituted or substituted amino" refers to —NR'R in which R' and R are independently hydrogen, alkyl, aryl, heteroaryl, aralkyl, heteroaralkyl, alkylcarbonyl, arylcarbonyl, heteroarylcarbonyl, alkoxycarbonyl, aryloxycarbonyl, aralkyloxycarbonyl, unsubstituted or substituted aminocarbonyl, alkylsulfonyl, cycloalkylsulfonyl, arylsulfonyl, heteroarylsulfonyl, aralkylsulfonyl, or heteroaralkylsulfonyl.

As used herein, "alkylthio" refers to —SR in which R is alkyl.

As used herein, "cycloalkylthio" refers to —SR in which R is cycloalkyl.

As used herein, "arylthio" refers to —SR in which R is aryl.

As used herein, "heteroarylthio" refers to —SR in which R is heteroaryl.

As used herein, "aralkylthio" refers to —SR in which R is aralkyl.

As used herein, "heteroaralkylthio" refers to —SR in which R is heteroaralkyl.

As used herein, "alkylsulfinyl" refers to —S(O)R in which R is alkyl.

As used herein, "cycloalkylsulfinyl" refers to —S(O)R in which R is cycloalkyl.

As used herein, "arylsulfinyl" refers to —S(O)R in which R is aryl.

As used herein, "heteroarylsulfinyl" refers to —S(O)R in which R is heteroaryl.

As used herein, "aralkylsulfinyl" refers to —S(O)R in which R is aralkyl.

As used herein, "heteroaralkylsulfinyl" refers to —S(O)R in which R is heteroaralkyl.

As used herein, "alkylsulfonyl" refers to —S(O)$_2$R in which R is alkyl.

As used herein, "cycloalkylsulfonyl" refers to —S(O)$_2$R in which R is cycloalkyl.

As used herein, "arylsulfonyl" refers to —S(O)$_2$R in which R is aryl.

As used herein, "heteroarylsulfonyl" refers to —S(O)$_2$R in which R is heteroaryl.

As used herein, "alkoxysulfonyl" refers to —S(O)$_2$R in which R is alkoxy.

As used herein, "aryloxysulfonyl" refers to —S(O)$_2$R in which R is aryloxy.

As used herein, "aralkylsulfonyl" refers to —S(O)$_2$R in which R is aralkyl.

As used herein, "heteroaralkylsulfonyl" refers to —S(O)$_2$R in which R is heteroaralkyl.

As used herein, "unsubstituted or substituted aminosulfonyl" refers to —S(O)$_2$NR'R in which R' and R are independently hydrogen, alkyl aryl, heteroaryl, aralkyl or heteroaralkyl.

As used herein, pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-yl-methylbenzimidazole, diethylamineand other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and inorganic salts, such as but not limited to, sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates, mesylates, and fumarates.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures.

As used herein, substantially pure means sufficiently homogeneous to appear free of readily detectable impurities as determined by standard methods of analysis, such as thin layer chromatography (TLC), gel electrophoresis, high performance liquid chromatography (HPLC), nuclear magnetic resonance (NMR), and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound. The instant disclosure is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

As used herein, the IC$_{50}$ refers to an amount, concentration or dosage of a particular test compound that achieves a 50% inhibition of a maximal response in an assay that measures such response.

As used herein, EC$_{50}$ refers to a dosage, concentration or amount of a particular test compound that elicits a dose-dependent response at 50% of maximal expression of a particular response that is induced, provoked or potentiated by the particular test compound.

As used herein, treatment means any manner in which one or more of the symptoms of a disease or disorder are ameliorated or otherwise beneficially altered. Treatment also encompasses any pharmaceutical use of the compositions herein, such as use for treating diabetes.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, the terms "preventing" means guard against the recurrence of the specified disease or disorder in a patient who has already suffered from the disease or disorder, and/or lengthening the time that a patient who has suffered from the disease or disorder remains in remission.

The terms "GSK-3 mediated disease, or "GSK-3 mediated condition", as used herein, mean any disease or other deleterious condition or state in which GSK-3 is known to play a role. Such diseases or conditions include, without limitation, diabetes, conditions associated with diabetes, chronic neurodegenerative conditions including dementias such as Alzheimer's disease, Parkinson's disease, progressive supranuclear palsy, subacute sclerosing panencephalitic parkinsonism, postencephalitic parkinsonism, pugilistic encephalitis, guam parkinsonism-dementia complex, Pick's disease, corticobasal degeneration, frontotemporal dementia, Huntington's Disease, AIDS associated dementia, amyotrophic lateral sclerosis, multiple sclerosis, neurotraumatic diseases such as acute stroke, epilepsy, mood disorders such as depression, schizophrenia and bipolar disorders, rheumatoid arthritis, inflammatory bowel disease, ulcerative colitis, Crohn's disease, sepsis, pancreatic cancer, ovarian cancer and osteoporosis.

B. Compounds

Provided herein are compounds of Formula (I):

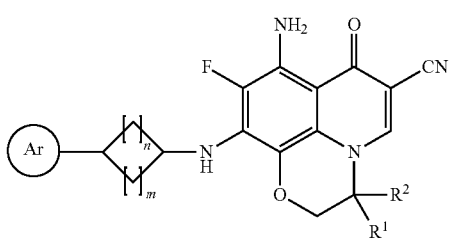

or a pharmaceutically acceptable salt thereof, wherein
R¹ is lower alkyl;
R² is hydrogen or lower alkyl;
m is 1, 2 or 3;
n is 1 or 2;
Ar is aryl or heteroaryl which is optionally substituted with one to three substituents, each independently selected from Q groups;
wherein Q is halo, hydroxy, cyano, nitro, oxo, thioxo, hydroxycarbonyl, alkyl, haloalkyl, alkenyl, alkynyl, cycloalkyl, heterocyclyl, aryl, heteroaryl, aralkyl, heteroaralkyl, alkoxy, haloalkoxy, cycloalkoxy, heterocyclyloxy, aryloxy, heteroaryloxy, aralkyloxy, heretoaralkyloxy, alkylcarbonyl, arylcarbonyl, heteroarylcarbonyl, alkoxycarbonyl, aryloxycarbonyl, aralkyloxycarbonyl, unsubstituted or substituted aminocarbonyl, alkylcarbonyloxy, arylcarbonyloxy, aralkylcarbonyloxy, alkoxycarbonyloxy, aryloxycarbonyloxy, aralkyloxycarbonyloxy, unsubstituted or substituted aminocarbonyloxy, unsubstituted or substituted amino, alkylthio, cycloalkylthio, arylthio, heteroarylthio, aralkylthio, heteroaralkylthio, alkylsulfinyl, cycloalkylsulfinyl, arylsulfinyl, heteroarylsulfinyl, aralkylsulfinyl, heteroaralkylsulfinyl, alkylsulfonyl, cycloalkylsulfonyl, arylsulfonyl, heteroarylsulfonyl, aralkylsulfonyl, heteroaralkylsulfonyl, alkoxysulfonyl, aryloxysulfonyl, unsubstituted or substituted aminosulfonyl, alkoxysulfonyl, aryloxysulfonyl, or hydroxysulfonyl; halo, cyano, nitro, NH₂, alkyl, haloalkyl, alkoxy or haloalkoxy.

In one embodiment, R² is hydrogen.

In another embodiment, Ar is heteroaryl which is optionally substituted with one to three substituents, each independently selected from Q groups.

In another embodiment, m+n is 3 or 4.

In certain embodiments, the compounds are of Formula (Ia):

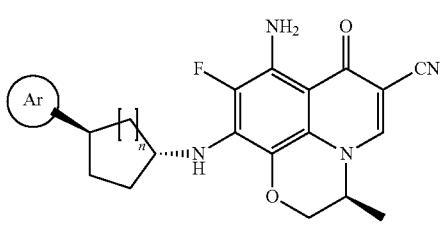

or a pharmaceutically acceptable salt thereof, wherein
n is 1 or 2;
Ar is aryl or heteroaryl which is optionally substituted with one to three substituents, each independently selected from Q groups;
wherein Q is halo, hydroxy, cyano, nitro, oxo, thioxo, hydroxycarbonyl, alkyl, haloalkyl, alkenyl, alkynyl, cycloalkyl, heterocyclyl, aryl, heteroaryl, aralkyl, heteroaralkyl, alkoxy, haloalkoxy, cycloalkoxy, heterocyclyloxy, aryloxy, heteroaryloxy, aralkyloxy, heretoaralkyloxy, alkylcarbonyl, arylcarbonyl, heteroarylcarbonyl, alkoxycarbonyl, aryloxycarbonyl, aralkyloxycarbonyl, unsubstituted or substituted aminocarbonyl, alkylcarbonyloxy, arylcarbonyloxy, aralkylcarbonyloxy, alkoxycarbonyloxy, aryloxycarbonyloxy, aralkyloxycarbonyloxy, unsubstituted or substituted aminocarbonyloxy, unsubstituted or substituted amino, alkylthio, cycloalkylthio, arylthio, heteroarylthio, aralkylthio, heteroaralkylthio, alkylsulfinyl, cycloalkylsulfinyl, arylsulfinyl, heteroarylsulfinyl, aralkylsulfinyl, heteroaralkylsulfinyl, alkylsulfonyl, cycloalkylsulfonyl, arylsulfonyl, heteroarylsulfonyl, aralkylsulfonyl, heteroaralkylsulfonyl, alkoxysulfonyl, aryloxysulfonyl, unsubstituted or substituted aminosulfonyl, or hydroxysulfonyl.

In one embodiment, the compounds are of Formula (Ia), wherein Ar is heteroaryl which is optionally substituted with one to three substituents, each independently selected from Q groups.

In one embodiment, the compounds are of Formula (Ia), wherein Ar is pyridyl, pyramidyl, pyrazolyl or imidazolyl, which is optionally substituted with one to three substituents, each independently selected from Q groups.

In another embodiment, the compound is selected from:

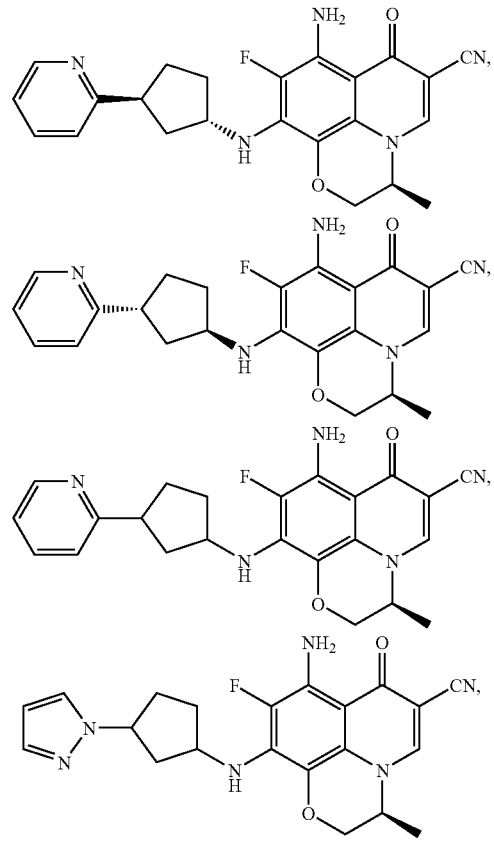

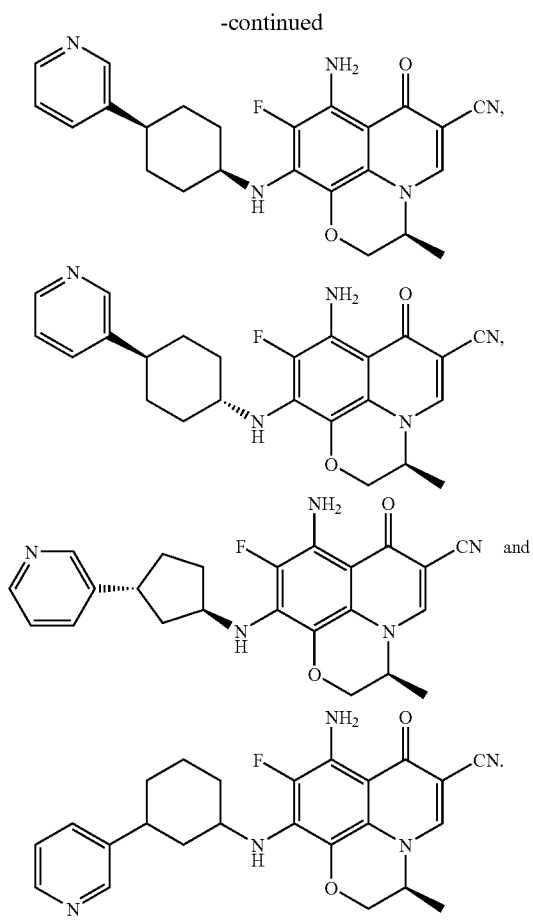

C. Preparation of the Compounds

The compounds provided herein can be prepared by methods known to one of skill in the art as showed below and following procedures similar to those described in the Examples section herein and routine modifications thereof.

Kyorin Pharmaceutical Co., Ltd., Japanese Unexamined Patent Publication S62-252772,
Ube Industries, Ltd., Japanese Unexamined Patent Publication S63-264439, Bayer AG, Japanese Unexamined Patent Publication H1-268679,
Ihara Chemical Industry Co., Ltd., Japanese Unexamined Patent Publication H10-70584,
Daiichi Seiyaku Co., Ltd., Japanese Unexamined Patent Publication S59-1489,
Tokyo Tanabe Co., Ltd., Japanese Unexamined Patent Publication S62-53987,
F. Hoffmann-La Roche Ltd., Japanese Unexamined Patent Publication S63-132891,
H. Koga et al., *J. Med. Chem.,* 1980, 23, 1358,
S. Atarashi et al., *Chem. Pharm. Bull.,* 1987, 35, 1896,
S. Atarashi et al., *J. Heterocyclic Chem.,* 1991, 28, 329,
H. Egawa et al., *Chem. Pharm. Bull.,* 1986, 34, 4098,
L. A. Mitscher et al., *J. Med. Chem.,* 1987, 30, 2283,
G. B. Mullen et al., *J. Med. Chem.,* 1988, 31, 1694,
J. S. Kiely et al., *J. Med. Chem.,* 1988, 31, 2004,
P. Remuzon et al., *J. Med. Chem.,* 1991, 34, 29,
Warner-Lambert Co., Japanese Unexamined Patent Publication S62-167769,
Shionogi Seiyaku Kk, Japanese Unexamined Patent Publication H5-25162,
Inke, S. A., ES 206819,
M. Kawatsura et al., *Tetrahedron,* 2007, 63, 4172,
T. Kaiho et al., *J. Med. Chem.,* 1989, 32, 351,
Y. Kobayashi et al., *Org. Lett.,* 2005, 7, 183 and
Y. Kobayashi et al., *Org. Lett.,* 2005, 7, 1319.

The compounds represented by the general formula (1) can be produced by Synthesis 1 or a combination of conventional methods.

Synthesis 1

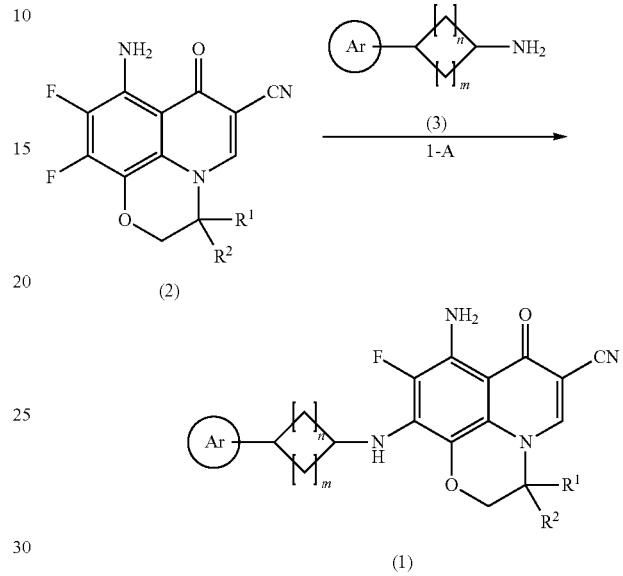

wherein Ar, $R^1R^2$, m and n are as described above.

The conversion from the general formula (2) and the general formula (3) to the general formula (1) (i.e., Process 1-A) is carried out at room temperature to 180° C. for 1-48 hours by using a base (such as triethylamine, pyridine, isopropylethylamine, and 1,8-diazabicycloundecyne) in a suitable solvent (such as N,N-dimethylformamide, dimethylsulfoxide, N-methylpyrrolidone, toluene, acetonitrile, tetrahydrofran, methanol, ethanol or a mixture thereof) or solvent-free.

The compounds represented by the general formula (1) can be produced by Synthesis 2 as well.

Synthesis 2

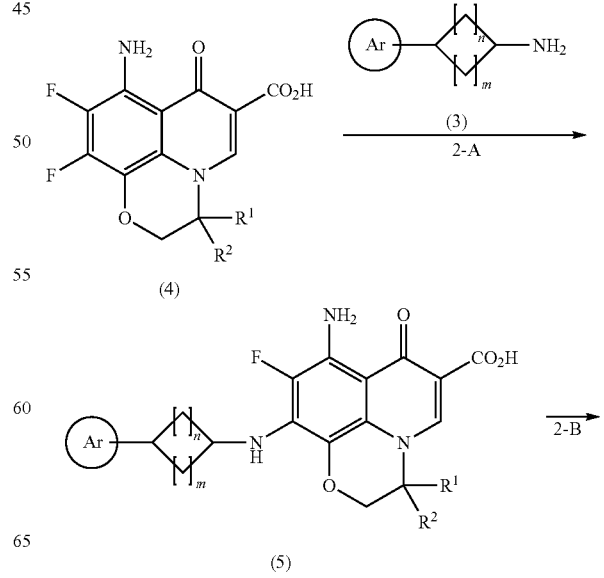

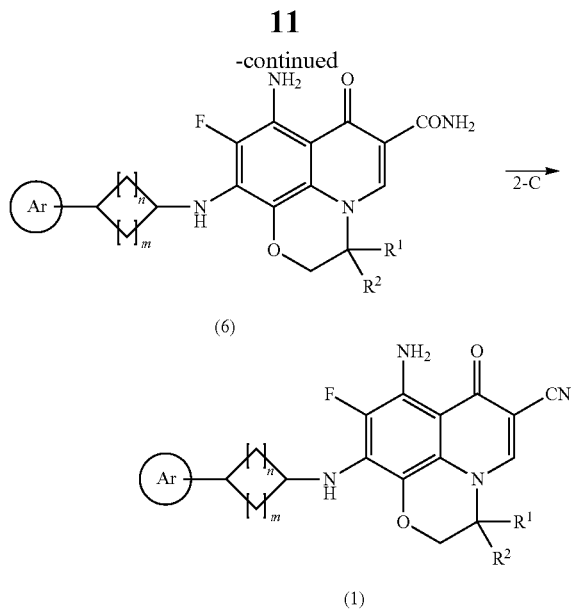

wherein Ar, $R^1R^2$, m and n are as described above.

The conversion from the general formula (4) to the general formula (5) (i.e., Process 2-A) can be performed by a method similar to Process 1-A.

The conversion from the general formula (5) to the general formula (6) (i.e., Process 2-B) can be carried out as follows: the general formula (5) is first reacted with thionyl chloride, thionyl bromide, acetic anhydride, ethyl chlorocarbonate, methyl chlorocarbonate, or the like in a suitable solvent (such as N,N-dimethylformamide, dichloromethane, chloroform, tetrahydrofuran or a mixture thereof) at −15° C. to room temperature for 5 min to 3 hours. This converts the carboxyl group to a reactive derivatizing group. The reaction can be carried out in the absence or in the presence of base (such as pyridine and triethylamine). Subsequently, the reaction product is reacted with ammonia aqueous solution in a suitable solvent (such as N,N-dimethylformamide, dichloromethane, chloroform, tetrahydrofuran or a mixture thereof) at a temperature from 0° C. to 100° C. for 30 min to 24 hours.

The conversion from the general formula (6) to the general formula (1) (i.e., Process 2-C) can be carried out as follows: the general formula (6) is reacted with a dehydroxylation reagent (such as trifluoroacetic anhydride and phosphorus oxychloride) in the presence of base (such as pyridine and triethylamine) in a suitable solvent (such as dichloromethane, chloroform, tetrahydrofuran or a mixture thereof) at −78° C. to 50° C. for 1-24 hours.

The compounds represented by the general formula (3) can be produced by Synthesis 3 as well.

Synthesis 3

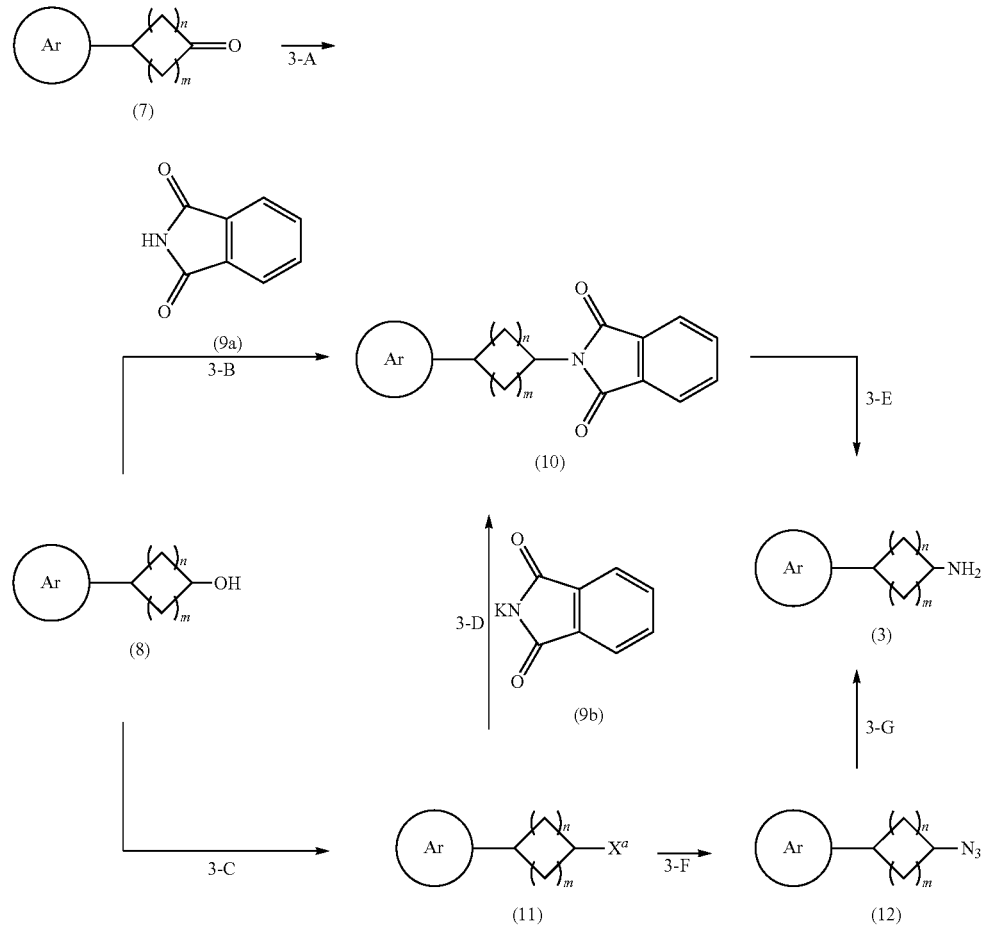

wherein Ar, m and n are as described above, and $X^a$ is leaving group (such as halogen atom, p-toluenesulfonyloxy group, methanesulfonyloxy group, trifluomethanesulfonyloxy group).

The conversion from the general formula (7) to the general formula (8) (i.e., Process 3-A) can be carried out at 0° C. to 50° C. for 30 min to 24 hours by using a reducing reagent (such as sodium borohydride, lithium borohydride, diisobutylaluminum hydride, lithium aluminum hydride) in a suitable solvent (such as tetrahydrofran, methanol, ethanol or a mixture thereof).

The conversion from the general formula (8) and the compound (9a) to the general formula (10) (i.e., Process 3-B) can be carried out at 0° C. to 50° C. for 1-24 hours by using a Mitsunobu reagent (such as diethyl azodicarboxylate, diisopropyl azodicarboxylate, cyanomethylenetributylphosphorane, N,N,N',N'-tetramethylazodicarboxamide) with phosphine reagent (such as triphenylphosphine, tributylphosphine) if need, in a suitable solvent (such as tetrahydrofran, 1,4-dioxane, toluenene, benzene, or a mixture thereof).

Alternatively, the conversion can be performed as follows: the general formula (8) to the general formula (11) (i.e., Process 3-C) can be carried out at 0° C. to room temperature for 1-24 hours by using halogenating agent (such as thionyl chloride, phosphorous oxychloride or thionyl bromide) or sulfonating agent (such as methanesulfonyl chloride, p-toluenesulfonyl chloride or trifluoromethanesulfonic acid anhydride) in the presence of a base (such as triethylamine, pyridine, isopropylethylamine, and 1,8-diazabicycloundecyne) in a suitable solvent (such as N,N-dimethylformamide, dimethylsulfoxide, toluene, acetonitrile, tetrahydrofran, dichloromethene or a mixture thereof).

Then the general formula (11) and the compound (9b) to the general formula (10) (i.e., Process 3-D) can be carried out at 0° C. to 100° C. for 1-12 hours in a suitable solvent (such as N,N-dimethylformamide, dimethylsulfoxide, N-methylpyrrolidone, toluene, acetonitrile, tetrahydrofran, methanol, ethanol or a mixture thereof).

The conversion from the general formula (10) to the general formula (3) (i.e., Process 3-E) can be carried out at 0° C. to 100° C. for 30 min-12 hours by using a hydrazine reagent (such as $NH_2NH_2$—$H_2O$, $MeNHNH_2$, $PhNHNH_2$), acid (such as hydrochloric acid, formic acid) or base (such as KOH, NaOH, $K_2CO_3$) in a suitable solvent (such as, methanol, ethanol, toluene, acetonitrile, tetrahydrofran, water or a mixture thereof).

Alternatively, the conversion can be performed as follows: the general formula (11) to the general formula (12) (i.e., Process 3-F) can be carried out with azidation reagent (such as sodium azide, trimethylsilylazide, diphenylphosphinyl azide) at room temperature to 80° C. for 1-24 hours in a suitable solvent (such as dimethylsulfoxide, toluenene, tetrahydrofuran, N,N-dimethylformamide, acetonitrile, dichloromethane or a mixture thereof). The conversion from the general formula (12) to the general formula (3) (i.e., Process 3-G) can performed by hydrogenation using metal catalyst (such as palladium on activated carbon, platinum on activated carbon, oxidized platinum and Raney nickel) in a suitable solvent (such as methanol, ethanol, ethyl acetate, tetrahydrofuran, N,N-dimethylformamide, acetic acid or a mixture thereof) at room temperature to 80° C. for 1-24 hours. The reaction can be carried out at a pressure from normal pressure to 0.5 MPa in hydrogen atmosphere.

In Synthesis 3, among the compounds represented by the general formula (7), a compounds represented by the general formula (7a) can be produced by Synthesis 4

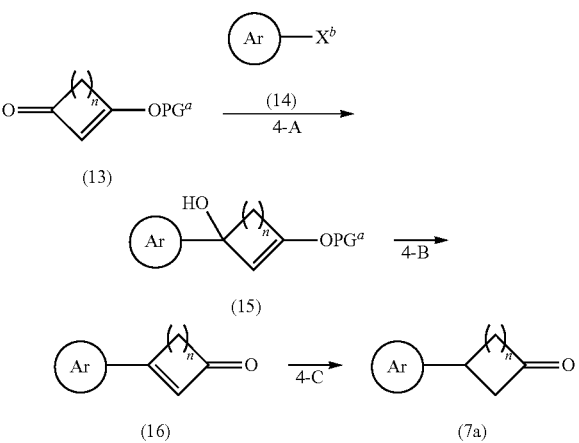

Synthesis 4 wherein Ar and n are as described above, and $PG^a$ is protecting group (such as Methyl, ethyl, benzyl, trimethylsilyl, acetyl) and $X^b$ is halogen atom.

The conversion from the general formula (13) and the general formula (14) to the general formula (15) (i.e., Process 4-A) can be performed as follows: the general formula (14) is reacted with alkyl lithium (such as n-Butyl lithium, i-Butyl lithium, t-Butyl lithium, Lithium diisopropylamine) at −78° C. to −40° C. for 10 min-1 hours in a suitable solvent (such as diethylether, tetrahydrofuran or a mixture thereof), and then the reaction product is reacted with the general formula (13) at −78° C. to room temperature for 1-12 hours in a suitable solvent (such as diethylether, tetrahydrofuran or a mixture thereof).

The conversion from the general formula (15) to the general formula (16) (i.e., Process 4-B) can be carried out at −10 to 50° C. for 30 min-12 hours in a suitable solvent (such as water, acetonitrile, tetrahydrofran, dichloromethane, water or a mixture thereof) in the presence of acid (such as hydrochloric acid, trifluoromethneacetic acid, formic acid).

The conversion from the general formula (16) to the general formula (7a) (i.e., Process 4-C) can performed by hydrogenation using metal catalyst (such as palladium on activated carbon, platinum on activated carbon, oxidized platinum and Raney nickel) in a suitable solvent (such as methanol, ethanol, ethyl acetate, tetrahydrofuran, N,N-dimethylformamide, acetic acid or a mixture thereof) at room temperature to 80° C. for 1-24 hours. The reaction can be carried out at a pressure from normal pressure to 0.5 MPa in hydrogen atmosphere.

In Synthesis 3, among the compounds represented by the general formula (7), a compounds represented by the general formula (7b) can be produced by Synthesis 5

Synthesis 5

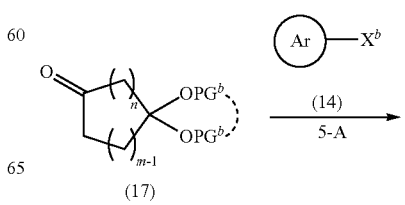

-continued

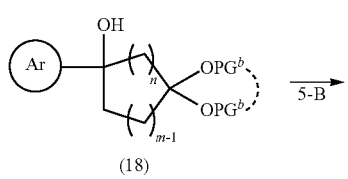

(18)

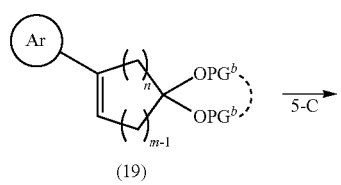

(19)

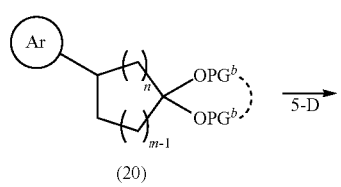

(20)

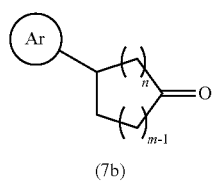

(7b)

wherein Ar, $X^b$, m and n are as described above, and $PG^b$ represents alkyl or aralkyl, or forms a cyclic ketal (such as 1,3-dioxane or 1,3-dioxolane).

The conversion from the general formula (17) and the general formula (14) to the general formula (18) (i.e., Process 5-A) can be performed by a method similar to Process 4-A.

The conversion the general formula (18) to the general formula (19) (i.e., Process 5-B) can be performed as follows: the general formula (18) is first reacted with halogenating reagent (thionyl chloride, phosphory chloride) or sulfonating reagent (methanesulfonyl chloride, p-toluenesulfonyl chloride) can be carried out at −10° C. to room temperature for 30 min to 5 hours in the presence of a base (such as triethylamine, pyridine, isopropylethylamine, and 1,8-diazabicycloundecyne) in a suitable solvent (such as toluene, acetonitrile, tetrahydrofran, dichloromethene or a mixture thereof).

Alternatively, the conversion can be carried out at room temperature to 100° C. for 30 min to 12 hours in a suitable solvent (such as water, acetonitrile, tetrahydrofran, dichloromethene or a mixture thereof) in the presence of a acid (such as hydrochloric acid, trifluoromethneacetic acid, formic acid).

The conversion from the general formula (19) to the general formula (20) (i.e., Process 5-C) can be performed by a method similar to Process 4-C.

The conversion from the general formula (20) to the general formula (7b) (i.e., Process 5-D) can be carried out at −10 to 50° C. for 30 min to 12 hours in a suitable solvent (such as water, acetonitrile, tetrahydrofran, dichloromethane, water or a mixture thereof) in the presence of acid (such as hydrochloric acid, trifluoromethneacetic acid, formic acid).

In Synthesis 3, among the compounds represented by the general formula (8), a compounds represented by the general formula (8a) can be produced by Synthesis 6.

Synthesis 6

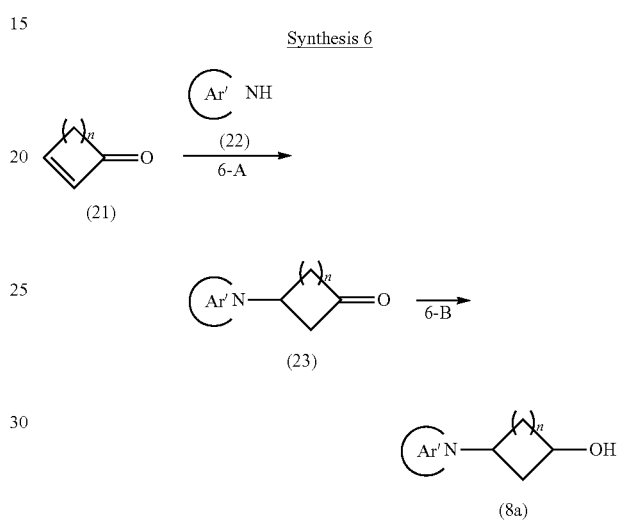

wherein n is as described above, and

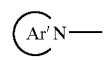

represents pyrroyl, imidazoyl, triazoyl or tetrazoyl which is optionally substituted with one to three substituents.

The conversion from the general formula (21) and the general formula (22) to the general formula (23) (i.e., Process 6-A) can be carried out at 0° C. to 50° C. for 30 min-24 hours by using a catalyst (such as NaOEt, AcOH, Copper reagent, Lewis acid) in a suitable solvent (such as tetrahydrofran, dichloromethane, toluene, diethylether, ethanol, acetnitrile).

The conversion from the general formula (23) to the general formula (8a) (i.e., Process 6-B) can be performed by a method similar to Process 3-A.

Among the compounds represented by the general formula (3), the compounds represented by the general formula (3b) and (3c) can be produced by Synthesis 7 as well.

Synthesis 7

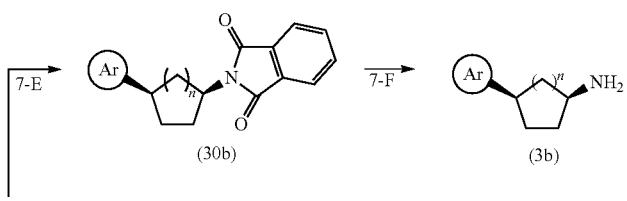

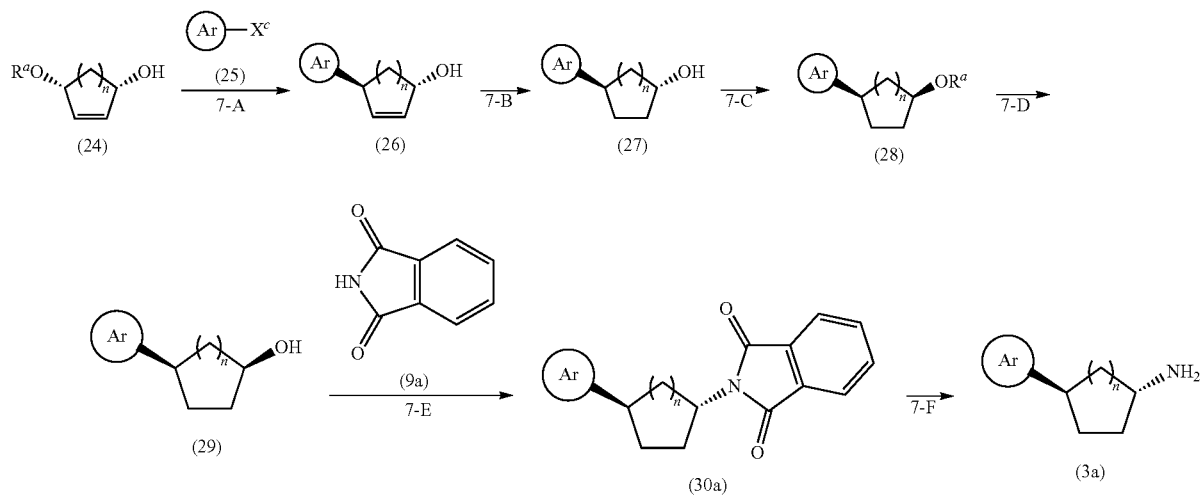

wherein Ar and n are as described above, and $X^c$ is halogen atom or halo magnesium (MgCl, MgBr, MgI), and $R^a$ is acyl group (such as formyl, acetyl or benzoyl)

The conversion from the general formula (24) and the general formula (25) to the general formula (26) (i.e., Process 7-A) can be performed as follows: when $X^c$ represents halogen atom, the general formula (25) is reacted with alkyl lithium (such as n-Butyl lithium, i-Butyl lithium, t-Butyl lithium) and Magnesium salt (such as $MgCl_2$) or Grignard reagent (such as i-PrMgCl, i-PrMgBr) at −78° C. to room temperature for 1-12 hours in the presence of Copper reagent (such as CuCN, CuI) in the in a suitable solvent (such as diethylether, tetrahydrofuran or a mixture thereof), and then the reaction product is reacted with the general formula (24) at −78° C. to room temperature for 1-12 hours in a suitable solvent (such as diethylether, tetrahydrofuran or a mixture thereof).

Alternatively, when $X^c$ represents or halo magnesium (MgCl, MgBr, MgI), the general formula (25) is reacted with Copper reagent (such as CuCN, CuI) at −78° C. to room temperature for 1-12 hours in a suitable solvent (such as diethylether, tetrahydrofuran or a mixture thereof), and then the reaction product is reacted with the general formula (24) at −78° C. to room temperature for 1-12 hours in a suitable solvent (such as diethylether, tetrahydrofuran or a mixture thereof).

The conversion from the general formula (26) to the general formula (27) (i.e., Process 7-B) can be performed by a method similar to Process 4-C.

The conversion from the general formula (27) to the general formula (28) (i.e., Process 7-C) can be carried out by a method similar to Process 3-B with acid reagent (such as acetic acid, trifluoroacetic acid, benzoic acid, p-nitrobenzoic acid).

The conversion from the general formula (28) to the general formula (29) (i.e., Process 7-D) can be carried at 0° C. to 50° C. for 1-24 hours in the presence of a base (such as $K_2CO_3$, NaOH, KOH, pyridine) in a suitable solvent (such as methanol, ethanol, tetrahydrofuran, water or a mixture thereof).

The conversion from the general formula (29) to the general formula (30a) or the general formula (27) to the general formula (30b) (i.e., Process 7-E) can be performed by a method similar to Process 3-B.

The conversion from the general formula (30a) to the general formula (3a) or the general formula (30b) to the general formula (3b) (i.e., Process 7-F) can be performed by a method similar to Process 3-E.

In Synthesis 1 and Synthesis 2, the compounds represented by the general formula (2) and (4) can be produced by Synthesis 8.

Synthesis 8

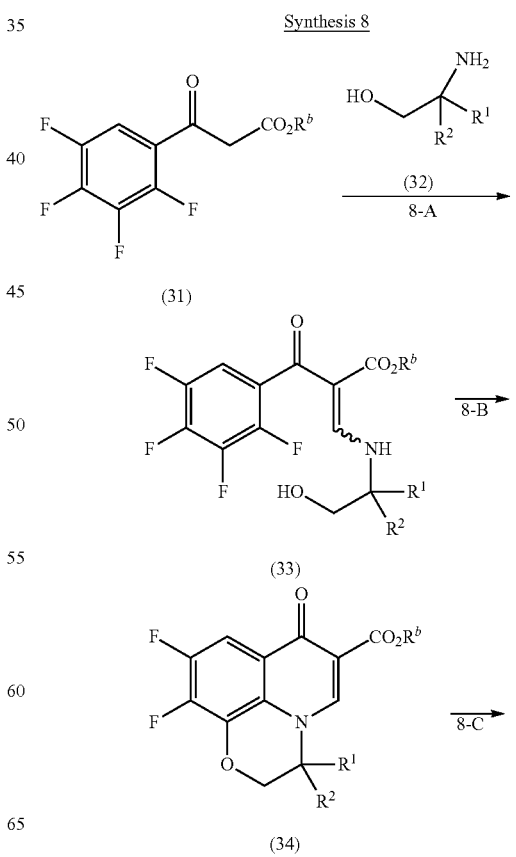

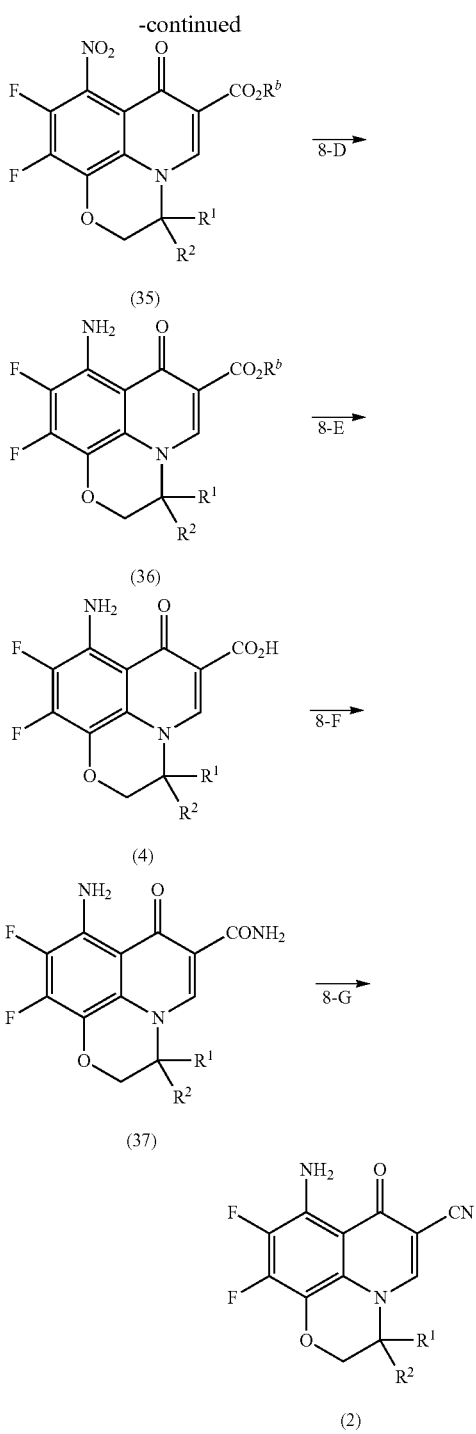

wherein $R^1$ and $R^2$ are as described above, and $R^b$ is alkyl (such as methyl, ethyl). The conversions from the general formula (31) and the general formula (32) to the general formula (33) (i.e., Process 8-A) can be performed as follows: the general formula (31) is reacted with a mixture of acetic anhydride and ortho-acid ester (such as ortho-formic acid ethyl ester and ortho-acetic ethyl ester) at 100° C. to 150° C. for 1-8 hours, and then the reaction product is reacted with the general formula (32) in a suitable solvent (such as toluene, tetrahydrofuran, methanol, ethanol, t-butanol, or a mixture thereof) at room temperature for 1-24 hours. The reaction can be carried out in the absence or in the presence of a base (potassium carbonate, sodium carbonate, t-BuOK, t-BuONa, triethylamine and pyridine).

The conversion from the general formula (33) to the general formula (34) (i.e., Process 8-B) can be carried out at 0° C. to 150° C. for 1-24 hours by using a base (such as potassium hydride, sodium hydride, potassium carbonate, sodium carbonate, t-BuOK and t-BuONa) or fluoride salt (such as potassium fluoride and sodium fluoride) in a suitable solvent (such as N,N-dimethylformamide, dimethylsulfoxide, tetrahydrofuran, or a mixture thereof).

The conversion from the general formula (34) to the general formula (35) (i.e., Process 8-C) can be conducted by general nitration, for instance, a reaction in concentrated sulfuric acid using a nitrosating reagent (such as potassium nitrate, sodium nitrate and nitric acid). The reaction can be carried out at 0° C. to 50° C. for 1-8 hours.

The conversion from the general formula (35) to the general formula (36) (i.e., Process 8-D) can be carried out at room temperature to 120° C. for 1-48 hours by using a metal (such as reduced iron, tin and zinc) in the presence of acid (such as hydrochloric acid and acetic acid) in a suitable solvent (such as tetrahydrofuran, methanol, ethanol, water or a mixture thereof) or solvent-free.

Alternatively, the conversion can be performed by hydrogenation using metal catalyst (such as palladium on activated carbon, platinum on activated carbon, oxidized platinum and Raney nickel) in a suitable solvent (such as methanol, ethanol, ethyl acetate, tetrahydrofuran, N,N-dimethylformamide, acetic acid or a mixture thereof) at room temperature to 80° C. for 1-24 hours. The reaction can be carried out at a pressure from normal pressure to 0.5 MPa in hydrogen atmosphere.

Furthermore, the conversion can be performed by reduction using sodium hydrosulfite in a suitable solvent (such as water, methanol, ethanol, tetrahydrofuran or a mixture thereof) at room temperature to 100° C. for 1-24 hours.

The conversion from the general formula (36) to the general formula (4) (i.e., Process 8-E) can be conducted by general hydrolysis, for instance, a reaction with alkali (such as KOH, NaOH, LiOH) or acid (such as hydrochloric acid, sulfuric acid, trifluoromethaneacetic acid) in a suitable solvent (such as water, methanol, ethanol, tetrahydrofuran or a mixture thereof). The reaction can be carried out at 0° C. to 50° C. for 1-8 hours.

The conversion from the general formula (4) to the general formula (37) (i.e., Process 8-F) can be performed by a method similar to Process 2-B.

The conversion from the general formula (37) to the general formula (2) (i.e., Process 8-G) can be performed by a method similar to Process 2-C.

Optical isomers of compounds represented by the general formula (1) may be synthesized using optically active material compounds according to the aforementioned Synthesis 1 to 3 and 7.

Racemic compounds represented by the general formula (1) may be synthesized by separation and recrystallization using optically active acid or base.

It may be produced by a chromatographic technique using a choral support.

D. Pharmaceutical Compositions

Provided herein are pharmaceutical compositions comprising a compound provided herein, e.g., a compound of Formula I, as an active ingredient, or a pharmaceutically acceptable salt thereof; in combination with a pharmaceutically acceptable vehicle, carrier, diluent, or excipient, or a mixture thereof.

The compound provided herein may be administered alone, or in combination with one or more other compounds provided herein. The pharmaceutical compositions that comprise a compound provided herein, e.g., a compound of Formula I, can be formulated in various dosage forms for oral, parenteral, and topical administration. The pharmaceutical compositions can also be formulated as modified release dosage forms, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Deliver Technology*, Rathbone et al., Eds., Drugs and the Pharmaceutical Science, Marcel Dekker, Inc.: New York, N.Y., 2003; Vol. 126).

In one embodiment, the pharmaceutical compositions are provided in a dosage form for oral administration, which comprise a compound provided herein, e.g., a compound of Formula I, or a pharmaceutically acceptable salt thereof; and one or more pharmaceutically acceptable excipients or carriers.

In another embodiment, the pharmaceutical compositions are provided in a dosage form for parenteral administration, which comprise a compound provided herein, e.g., a compound of Formula I, or a pharmaceutically acceptable salt thereof and one or more pharmaceutically acceptable excipients or carriers.

In yet another embodiment, the pharmaceutical compositions are provided in a dosage form for topical administration, which comprise a compound provided herein, e.g., a compound of Formula I, or a pharmaceutically acceptable salt thereof and one or more pharmaceutically acceptable excipients or carriers.

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In one embodiment, the therapeutically effective dose is from about 0.1 mg to about 2,000 mg per day of a compound provided herein. The pharmaceutical compositions therefore should provide a dosage of from about 0.1 mg to about 2000 mg of the compound. In certain embodiments, pharmaceutical dosage unit forms are prepared to provide from about 1 mg to about 2000 mg, from about 10 mg to about 1000 mg, from about 20 mg to about 500 mg or from about 25 mg to about 250 mg of the essential active ingredient or a combination of essential ingredients per dosage unit form. In certain embodiments, the pharmaceutical dosage unit forms are prepared to provide about 10 mg, 20 mg, 25 mg, 50 mg, 100 mg, 250 mg, 500 mg, 1000 mg or 2000 mg of the essential active ingredient.

Oral Administration

The pharmaceutical compositions provided herein can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, troches, lozenges, pastilles, cachets, pellets, medicated chewing gum, bulk powders, effervescent or non-effervescent powders or granules, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

The pharmaceutical compositions provided herein can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein can be formulated as immediate or modified release dosage forms, including delayed-, sustained, pulsed-, controlled, targeted-, and programmed-release forms.

The pharmaceutical compositions provided herein can be co-formulated with other active ingredients which do not impair the desired therapeutic action, or with substances that supplement the desired action.

Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions provided herein can be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein can be formulated as immediate or modified release dosage forms, including delayed-, sustained, pulsed-, controlled, targeted-, and programmed-release forms.

The pharmaceutical compositions can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein, a propellant as solvent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator can be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include dextran, glucose, maltose, sorbitol, xylitol, fructose, sucrose, and trehalose. The pharmaceutical compositions provided herein for inhaled/intranasal administration can further comprise a suitable flavor, such as menthol and levomenthol, or sweeteners, such as saccharin or saccharin sodium.

The pharmaceutical compositions provided herein for topical administration can be formulated to be immediate release or modified release, including delayed-, sustained-, pulsed-, controlled-, targeted, and programmed release.

Modified Release

The pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form can be fabricated using a matrix controlled release device known to those skilled in the art (see, Takada et al in "Encyclopedia of Controlled Drug Delivery," Vol. 2, Mathiowitz Ed., Wiley, 1999).

In one embodiment, the pharmaceutical compositions provided herein in a modified release dosage form is formulated using an erodible matrix device, which is water-swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(–)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In further embodiments, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethylene terephthalate, natural rubber, silicone rubbers, polydimethylsiloxanes, silicone carbonate copolymers, and; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, melt-granulation followed by compression.

2. Osmotic Controlled Release Devices

The pharmaceutical compositions provided herein in a modified release dosage form can be fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly (acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly (acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxyethyl cellulose, and other pharmaceutically acceptable excipients or carriers.

3. Multiparticulate controlled release devices

The pharmaceutical compositions provided herein in a modified release dosage form can be fabricated as a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates can be made by the processes known to those skilled in the art, including wet-and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical compositions provided herein can also be formulated to be targeted to a particular tissue, receptor, or other area of the body of the subject to be treated, including liposome-, resealed erythrocyte-, and antibody-based delivery systems. Examples include, but are not limited to, U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Articles of Manufacture

The compounds or pharmaceutically acceptable salts can be packaged as articles of manufacture containing packaging material, a compound or pharmaceutically acceptable salt thereof provided herein, which is used for treatment, prevention or amelioration of one or more symptoms associated with kinase activity, including, but not limited to, GSK-3 activity, and a label that indicates that the compound or pharmaceutically acceptable salt thereof is used for treatment, prevention or amelioration of one or more symptoms of kinase-mediated, including, but not limited to, GSK-3-mediated diseases.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated.

E. Methods of Treatment

Methods of use of the compounds and compositions are also provided. The methods involve both in vitro and in vivo uses of the compounds and compositions.

In certain embodiments, provided herein are methods for inhibiting the action of GSK-3 by administering compounds and compositions provided herein. In one embodiment, the methods involve contacting GSK-3 with a compound provided herein.

F. Evaluation of Compound Activity

A) GSK Inhibition

GSK3 inhibitory activity of the compounds provided herein can be readily detected using the assays described herein, as well as assays generally known to those of ordinary skill in the art.

Exemplary methods for identifying specific inhibitors of GSK3 include both cell-free and cell-based GSK3 kinase assays. A cell-free GSK3 kinase assay detects inhibitors that act by direct interaction with the polypeptide GSK3, while a cell-based GSK3 kinase assay may identify inhibitors that function either by direct interaction with GSK3 itself, or by interference with GSK3 expression or with post-translational processing required to produce mature active GSK3. U.S. Application No. 20050054663 describes exemplary cell-free and cell-based GSK3 kinase assays. Exemplary assays used herein are discussed briefly below:

10-25 ng of recombinant full-length human GSK3β (Upstate) is incubated in the presence or absence of compound at varying concentrations for 1 hour at 30 degrees Celsius in 20 mM MOPS, pH 7.0, 10 mM magnesium acetate, 0.2 mM EDTA, 2 mM EGTA, 30 mM magnesium chloride, 62.5 μM phospho-glycogen synthase peptide-2, 5 μM ATP, 10 mM β-glycerol phosphate, 1 mM sodium orthovanadate and 1 mM dithiothreitol. Proceed to KinaseGlo luciferase reaction.

Following the completion of the kinase reaction an equal volume of KinaseGlo luciferase reagent (Promega) is added and the luminescence read using a luminescence plate reader within 5-10 minutes. Compound activity is expressed as % inhibition relative to maximal inhibition observed at the maximal dose and $IC_{50}$ values then calculated using curve fitting software (GraphPad Prizm).

B) GS Activation

HepG2 cells were obtained from the Japanese Collection of Research Bioresources and were grown in standard culture medium, a low-glucose Dulbecco's modified Eagle's medium (DMEM) containing 10% fetal calf serum supplemented with 100 U/mL penicillin and 100 μg/mL streptomycin, in a humidified and 5% $CO_2$ atmosphere kept at 37° C. The HepG2 cells were harvested with 0.25% trypsin solution containing 1 mM EDTA, and were seeded on 12 well plates at $1\times10^5$ cells per well. Following a culture for 3 days, the cells were washed once with phosphate buffered saline (PBS), and were incubated with serum-free low-glucose DMEM supplemented with 100 U/mL penicillin and 100 μg/mL streptomycin. Following a culture for 3 hrs, GSK-3 inhibitor at various concentration and 2.5 μCi/mL D-[2-$^3$H]glucose (New England Nuclear, Boston, Mass., USA) were added to the serum-free low-glucose DMEM. A vehicle control of DMSO (0.3%, final concentration) was also used. Total volume per well of the reaction medium was 1.0 mL of serum-free low-glucose DMEM. After incubation at 37° C. for 3 hrs, medium was aspirated and cells were washed twice with PBS, and were added 0.25 mL of 1 N KOH containing 0.4 mg/mL carrier glycogen. After incubation at 37° C. for 30 min, 0.25 mL of 48.8% (w/v) KOH was added to well for cell lysis. After incubation at 95° C. for 30 min, 1.5 mL of 95% (v/v) ethanol was added to the cell lysate. Total glycogen was precipitated overnight at −20° C. Glycogen precipitates were recovered by centrifugation at 19,000×g for 30 min at 4° C. Precipitates were washed once with 1 mL of 70% (v/v) ethanol, and were re-suspended in 0.5 mL water. [$^3$H]Glucose incorporation into glycogen was assessed using a liquid scintillation counter (Packard Instrument Co., Meriden, Conn., USA).

It is understood that the foregoing detailed description and accompanying examples are merely illustrative, and are not to be taken as limitations upon the scope of the subject matter. Various changes and modifications to the disclosed embodiments will be apparent to those skilled in the art. Such changes and modifications, including without limitation those relating to the methods of use provided herein, may be made without departing from the spirit and scope thereof. Patents, patent publications, and other publications referenced herein are incorporated by reference.

EXAMPLES

Example 1

(3S)-8-amino-9-fluoro-2,3-dihydro-3-methyl-7-oxo-10-[(1S,3S)-3-(2-pyridyl)cyclopentylamino]-7H-pyrido[1,2,3-de][1,4]benzoxazine-6-carbonitrile Step 1: 3-(2-pyridyl)-2-cyclopenten-1-one

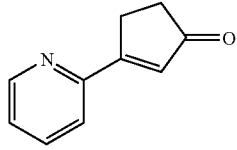

To a solution of 2-Bromopyridine (5.00 g, 31.6 mmol) in THF (30 ml) was added dropwise n-BuLi (2.55 M in Hexane, 12.5 mL. 31.9 mmol) at −78° C., and stirred for 10 min. To a reaction mixture was added dropwise 3-ethoxy-2-cyclopentenone (2.00 g, 15.9 mmol) in THF (10 mL) at −78° C., and stirred at 0° C. for 2 h. The reaction mixture was acidified with 2M HCl (10 mL), and aqueous layer was washed with EtOAc. The aqueous layer was basified with 1M NaOH aq., and then extracted with $CH_2Cl_2$. The organic layer was washed with brine, and dried over anhyd $Na_2SO_4$ followed by the removal of solvent. The crude product was purified by column chromatography (Hexane/EtOAc=1/3) to yield 3-(2-pyridyl)-2-cyclopenten-1-one (1.57 g, 58%) as brown solid.

$^1$H-NMR (CDCl$_3$-d, 400 MHz) δ 2.60-2.65 (2H, m), 3.16 (2H, dt, J=7.9, 1.8 Hz), 6.82 (1H, t, J=1.8 Hz), 7.32-7.37 (1H, m), 7.70 (1H, d, J=7.9 Hz), 7.79 (1H, td, J=7.9, 1.8 Hz), 8.73 (1H, d, J=4.9 Hz).

EIMS (+) 159 [M]$^+$.

Step 2: 3-(2-pyridyl)cyclopentan-1-one

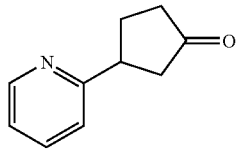

A mixture of 3-(2-pyridyl)-2-cyclopenten-1-one (1.43 g, 8.98 mmol) and 10% Pd/C (142 mg) in EtOH (30 mL) was stirred under hydrogen atmosphere (0.3 MPa) for 6.5 h. The catalyst was removed by filtration over Celite and the filtrate was concentrated in vacuo. The crude product was purified by column chromatography (Hexane/EtOAc=1/1) to yield 3-(2-pyridyl)cyclopentan-1-one (3.26 g, 94%) as colorless oil.

$^1$H-NMR (CDCl$_3$-d, 400 MHz) δ 2.13-2.24 (1H, m), 2.26-2.35 (1H, m), 2.36-2.55 (2H, m), 2.56-2.75 (2H, m), 3.56 (1H, qui, J=6.7 Hz), 7.10-7.23 (2H, m), 7.64 (1H, td, J=7.3, 1.2 Hz), 8.57 (1H, d, J=4.2 Hz).

EIMS (+) 161 [M]$^+$.

Step 3: cis-3-(2-pyridyl)cyclopentanol

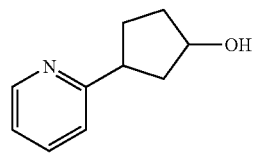

To a solution of 3-(2-pyridyl)cyclopentan-1-one (3.17 g, 19.7 mmol) in MeOH (80 ml) was added portionwise NaBH$_4$ (745 mg. 19.7 mmol) at 0° C., and stirred for 2 h at room temperature. The reaction mixture was poured into ice-water and then extracted with EtOAc. The organic layer was dried over anhyd Na$_2$SO$_4$ followed by the removal of solvent. The crude product was purified by column chromatography (Hexane/EtOAc=1/1→1/3) to yield cis-3-(2-pyridyl)cyclopentanol (1.90 g, 59%) as colorless oil.

$^1$H-NMR (CDCl$_3$-d, 400 MHz) δ 1.70-2.00 (4H, m), 2.12-2.30 (2H, m), 3.42 (1H, dd, J=15.2, 9.7 Hz), 4.35 (1H, t, J=4.3 Hz), 6.47 (1H, brs), 7.10 (1H, dd, J=7.3, 5.5 Hz), 7.17 (1H, d, J=7.3 Hz), 7.59 (1H, t, J=7.3 Hz), 8.51 (1H, d, J=4.3 Hz).

EIMS (+) 163 [M]$^+$.

Step 4: trans-N-[3-(2-pyridyl)cyclopentyl]phthalimide

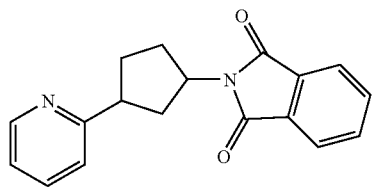

A solution of cis-3-(2-pyridyl)cyclopentanol (1.86 g, 11.4 mmol) in THF (100 mL) was cooled to 0° C. and treated with phthalimide (1.85 g, 12.5 mmol), diethylazodicarboxylate (2.2 M in toluene, 5.7 mL, 11.4 mmol) and triphenylphosphine (3.29 g, 12.5 mmol). The reaction mixture was stirred at room temperature for overnight. The solvent was removed, and the crude product was purified by column chromatography (Hexane/EtOAc=3/1→2/1→1/1) to yield trans-N-[3-(2-pyridyl)cyclopentyl]phthalimide (1.52 g, 41%) as a colorless powder.

$^1$H-NMR (CDCl$_3$-d, 400 MHz) δ 1.87-2.02 (1H, m), 2.15-2.41 (4H, m), 2.47 (1H, ddd, J=13.4, 8.6, 6.1 Hz), 3.81 (1H, qui, J=8.6 Hz), 4.92-5.03 (1H, m), 7.11 (1H, dd, J=7.3, 5.2 Hz), 7.22 (1H, d, J=7.3 Hz), 7.60 (1H, td, J=7.3, 1.2 Hz), 7.69-7.73 (2H, m), 7.81-7.85 (2H, m), 8.57 (1H, d, J=4.3 Hz).

EIMS (+) 292 [M]$^+$.

Step 5: (1S,3S)-N-[3-(2-pyridyl)cyclopentyl]phthalimide and (1R,3R)-N-[3-(2-pyridyl)cyclopentyl]phthalimide

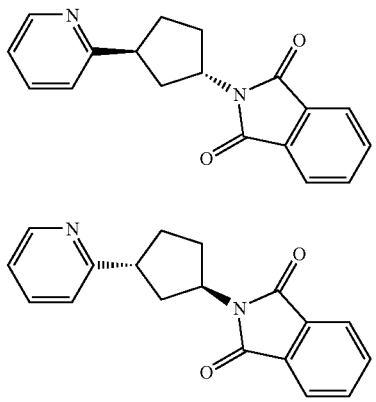

Trans-N-[3-(2-pyridyl)cyclopentyl]phthalimide (10.0 g) was separated by preparative HPLC using a Chiralpak IA column (φ20×250 mm) and MeCN—CH$_2$Cl$_2$ (9/1) as the eluent at a flow rate 5 mL/min for 1 h. The UV detector was set at 300 nm, the injection loop volume was 5 mL, and the injection load was 68-70 mg in a MeCN—CH$_2$Cl$_2$ (9/1) solution.

(1S,3S)-N-[3-(2-pyridyl)cyclopentyl]phthalimide; 4.78 g, >99% purify with >99% e.e. (Chiralpak IA column (φ4.6×250 mm), MeCN—CH$_2$Cl$_2$ (9/1), 0.5 mL/min, Rt=10.3 min)

(1R,3R)-N-[3-(2-pyridyl)cyclopentyl]phthalimide; 4.85 g, >99% purify with >99% e.e. (Chiralpak IA column (φ4.6×250 mm), MeCN—CH$_2$Cl$_2$ (9/1), 0.5 mL/min, Rt=13.4 min)

Step 6: (1S,3S)-3-(2-pyridyl)cyclopentylamine

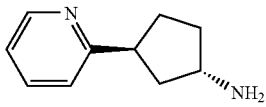

A mixture of (1S,3S)-N-[3-(2-pyridyl)cyclopentyl]phthalimide (4.12 g, 14.1 mmol), and hydrazinemonohydorate (2.0 mL, 41.2 mmol) in EtOH (100 mL) was stirred at reflux for 3 h. After cooling, the reaction mixture was filtered followed by the removal of solvent. The residue was suspended in EtOAc and stirred at reflux for 1 h. After cooling, the precipitate was filtered followed by the removal of solvent to yield (1S,3S)-3-(2-pyridyl)cyclopentylamine (2.10 g, 92%) as yellow oil.

$^1$H-NMR (CDCl$_3$-d, 400 MHz) δ 1.40-1.63 (3H, m), 1.77-1.92 (2H, m), 2.10-2.28 (3H, m), 3.49 (1H, qui, J=8.6 Hz), 3.66 (1H, qui, J=6.1 Hz), 7.08 (1H, dd, J=7.9, 5.5 Hz), 7.16 (1H, d, J=7.9 Hz), 7.57 (1H, td, J=7.9, 1.2 Hz), 8.54 (1H, d, J=4.3 Hz).

CIMS (+) 163 [M+H]$^+$.

Step 7: (3S)-8-amino-9-fluoro-2,3-dihydro-3-methyl-7-oxo-10-[(1S,3S)-3-(2-pyridyl)cyclopentylamino]-7H-pyrido[1,2,3-de][1,4]benzoxazine-6-carbonitrile

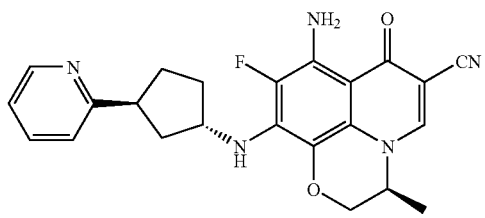

A mixture of (3S)-8-amino-9,10-difluoro-2,3-dihydro-3-methyl-7-oxo-7H-pyrido[1,2,3-de][1,4]benzoxazine-6-carbonitrile (1.30 g, 4.69 mmol), (1S,3S)-3-(2-pyridyl)cyclopentylamine (913 mg, 5.63 mmol) and triethylamine (1.30 mL, 9.33 mmol) in anhydrous DMSO (8 mL) was stirred at 100° C. for 7 h. After cooling, the reaction mixture was poured into ice-water and then extracted with CH$_2$Cl$_2$-MeOH. The organic layer was washed with water and brine, and dried over anhyd Na$_2$SO$_4$ followed by the removal of solvent. The crude product was purified by column chromatography (EtOAc) to yield (3S)-8-amino-9-fluoro-2,3-dihydro-3-methyl-7-oxo-10-[(1S,3S)-3-(2-pyridyl)cyclopentylamino]-7H-pyrido[1,2,3-de][1,4]benzoxazine-6-carbonitrile (364 mg, 19%) as a yellow powder.

$^1$H-NMR (DMSO-d$_6$, 400 MHz) δ 1.35 (3H, d, J=6.7 Hz), 1.66-1.82 (2H, m), 1.96-2.06 (1H, m), 2.06-2.20 (3H, m), 3.43 (1H, t, J=8.3 Hz), 4.05 (1H, dd, J=11.0, 1.8 Hz), 4.32 (1H, dd, J=11.0, 1.8 Hz), 4.39-4.52 (2H, m), 5.17 (1H, dd, J=7.9, 1.8 Hz), 6.94 (2H, brs), 7.17 (1H, dd, J=7.9, 4.9 Hz), 7.26 (1H, d, J=7.9 Hz), 7.67 (1H, td, J=7.9, 1.8 Hz), 8.46 (1H, s), 8.48 (1H, d, J=4.3 Hz).

ESIMS (+) 420 [M+H]$^+$.

HRESIMS (+) 420.18345 (Calcd for C$_{23}$H$_{23}$FN$_5$O$_2$, 420.18358).

anal. C, 65.57%; H, 5.24%; N, 16.31%. Calcd for C$_{23}$H$_{22}$FN$_5$O$_2$, 0.2H$_2$O, C, 65.30%; H, 5.34%; N, 16.55%.

Example 2

(3S)-8-amino-9-fluoro-2,3-dihydro-3-methyl-7-oxo-10-[(1R,3R)-3-(2-pyridyl)cyclopentylamino]-1-7H-pyrido[1,2,3-de][1,4]benzoxazine-6-carbonitrile

Step 1: (1R,3R)-3-(2-pyridyl)cyclopentylamine

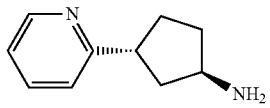

A mixture of (1R,3R)-N-[3-(2-pyridyl)cyclopentyl]phthalimide (4.17 g, 14.3 mmol), and hydrazinemonohydorate (2.0 mL, 41.2 mmol) in EtOH (100 mL) was stirred at reflux for 4 h. After cooling, the reaction mixture was filtered followed by the removal of solvent. The residue was suspended in EtOAc and stirred at reflux for 1 h. After cooling, the precipitate was filtered followed by the removal of solvent to yield (1R,3R)-3-(2-pyridyl)cyclopentylamine (1.62 g, 70%) as yellow oil.

¹H-NMR (CDCl₃-d, 400 MHz) δ 1.40-1.63 (3H, m), 1.77-1.92 (2H, m), 2.10-2.28 (3H, m), 3.49 (1H, qui, J=8.6 Hz), 3.66 (1H, qui, J=6.1 Hz), 7.08 (1H, dd, J=7.9, 5.5 Hz), 7.16 (1H, d, J=7.9 Hz), 7.57 (1H, td, J=7.9, 1.2 Hz), 8.54 (1H, d, J=4.3 Hz).

CIMS (+) 163 [M+H]⁺.

Step 2: (3S)-8-amino-9-fluoro-2,3-dihydro-3-methyl-7-oxo-10-[(1R,3R)-3-(2-pyridyl)cyclopentylamino]-7H-pyrido[1,2,3-de][1,4]benzoxazine-6-carbonitrile

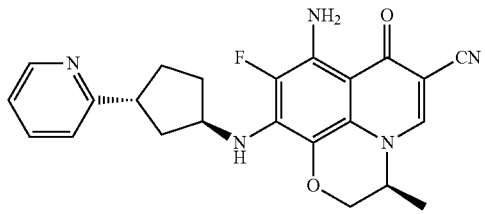

A mixture of (3S)-8-amino-9,10-difluoro-2,3-dihydro-3-methyl-7-oxo-7H-pyrido[1,2,3-de][1,4]benzoxazine-6-carbonitrile (1.40 g, 5.05 mmol), (1R,3R)-3-(2-pyridyl)cyclopentylamine (985 mg, 6.07 mmol) and triethylamine (1.40 mL, 10.0 mmol) in anhydrous DMSO (8 mL) was stirred at 100° C. for 7 h. After cooling, the reaction mixture was poured into ice-water and then extracted with CH₂Cl₂-MeOH. The organic layer was washed with water and brine, and dried over anhyd Na₂SO₄ followed by the removal of solvent. The crude product was purified by column chromatography (EtOAc) to yield (3S)-8-amino-9-fluoro-2,3-dihydro-3-methyl-7-oxo-10-[(1R,3R)-3-(2-pyridyl)cyclopentylamino]-7H-pyrido[1,2,3-de][1,4]benzoxazine-6-carbonitrile (325 mg, 15%) as a yellow powder.

¹H-NMR (DMSO-d₆, 400 MHz) δ 1.35 (3H, d, J=6.7 Hz), 1.66-1.82 (2H, m), 1.95-2.04 (1H, m), 2.05-2.23 (3H, m), 3.42 (1H, qui, J=7.9 Hz), 4.06 (1H, dd, J=11.0, 1.8 Hz), 4.33 (1H, dd, J=11.0, 1.8 Hz), 4.40-4.52 (2H, m), 5.17 (1H, dd, J=7.9, 1.8 Hz), 6.94 (2H, brs), 7.17 (1H, dd, J=7.3, 4.9 Hz), 7.26 (1H, d, J=7.9 Hz), 7.67 (1H, td, J=7.3, 1.8 Hz), 8.46 (1H, s), 8.48 (1H, d, J=4.3 Hz).

ESIMS (+) 420 [M+H]⁺.

HRESIMS (+) 420.18368 (Calcd for C₂₃H₂₃FN₅O₂, 420.18358).

anal. C, 65.61%; H, 5.28%; N, 16.19%. Calcd for C₂₃H₂₂FN₅O₂, C, 65.86%; H, 5.29%; N, 16.70%.

Example 3

(3S)-8-amino-9-fluoro-2,3-dihydro-3-methyl-7-oxo-10-[cis-3-(2-pyridyl)cyclopentylamino]-7H-pyrido[1,2,3-de][1,4]benzoxazine-6-carbonitrile Step 1: trans-3-(2-pyridyl)cyclopentanol

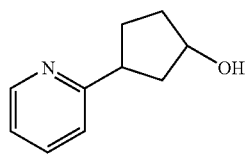

To a solution of 3-(2-pyridyl)cyclopentan-1-one (3.17 g, 19.7 mmol) in MeOH (80 ml) was added portionwise NaBH₄ (745 mg. 19.7 mmol) at 0° C., and stirred for 2 h at room temperature. The reaction mixture was poured into ice-water and then extracted with EtOAc. The organic layer was dried over anhyd Na₂SO₄ followed by the removal of solvent. The crude product was purified by column chromatography (Hexane/EtOAc=1/1→1/3) to yield trans-3-(2-pyridyl)cyclopentanol (965 mg, 30%) as colorless oil.

¹H-NMR (CDCl₃-d, 400 MHz) δ 1.50-1.78 (2H, m), 1.80-1.93 (1H, m), 2.04-2.13 (2H, m), 2.16-2.33 (2H, m), 3.55 (1H, qui, J=7.9 Hz), 4.52-4.62 (1H, m), 7.09 (1H, dd, J=7.3, 5.5 Hz), 7.17 (1H, d, J=7.3 Hz), 7.58 (1H, td, J=7.3, 1.8 Hz), 8.54 (1H, d, J=4.3 Hz).

EIMS (+) 163 [M]⁺.

Step 2: cis-N-[3-(2-pyridyl)cyclopentyl]phthalimide

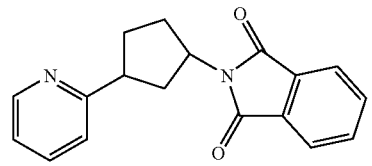

A solution of trans-3-(2-pyridyl)cyclopentanol (957 mg, 5.86 mmol) in THF (25 mL) was cooled to 0° C. and treated with phthalimide (1.29 g, 8.77 mmol), cyanomethylenetri-n-butylphosphorane (2.12 g, 8.78 mmol). The reaction mixture was stirred at 70° C. for 8 h. The solvent was removed, and the crude product was purified by column chromatography (Hexane/EtOAc=3/1→1/1) and triturated with Hexane-EtOAc to yield cis-N-[3-(2-pyridyl)cyclopentyl]phthalimide (901 mg, 53%) as a pale yellow powder.

¹H-NMR (CDCl₃-d, 400 MHz) δ 2.10-2.40 (5H, m), 2.56 (1H, dd, J=22.6, 12.2 Hz), 3.28-3.40 (1H, m), 4.80-4.90 (1H, m), 7.13 (1H, dd, J=7.9, 5.9 Hz), 7.35 (1H, d, J=7.9 Hz), 7.63 (1H, t, J=7.9 Hz), 7.71 (2H, dd, J=5.5, 3.0 Hz), 7.83 (2H, dd, J=5.5, 3.0 Hz), 8.55 (1H, d, J=4.3 Hz).

EIMS (+) 292 [M]⁺.

Step 3: cis-3-(2-pyridyl)cyclopentylamine

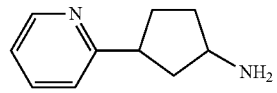

The title compound (498 mg, 99%) was prepared from cis-N-[3-(2-pyridyl)cyclopentyl]phthalimide (905 mg, 3.10 mmol) in a manner similar to that described for the preparation of trans-3-(2-pyridyl)cyclopentylamine.

¹H-NMR (CDCl₃-d, 400 MHz) δ 1.52-1.74 (3H, m), 1.95-2.13 (3H, m), 2.31-2.40 (1H, m), 3.26 (1H, qui, J=7.9 Hz), 3.48 (1H, qui, J=6.1 Hz), 7.09 (1H, dd, J=7.9, 4.9 Hz), 7.18 (1H, d, J=7.9 Hz), 7.58 (1H, td, J=7.9, 1.2 Hz), 8.54 (1H, d, J=4.3 Hz).

CIMS (+) 163 [M+H]⁺.

Step 4: (3S)-8-amino-9-fluoro-2,3-dihydro-3-methyl-7-oxo-10-[cis-3-(2-pyridyl)cyclopentylamino]-7H-pyrido[1,2,3-de][1,4]benzoxazine-6-carbonitrile

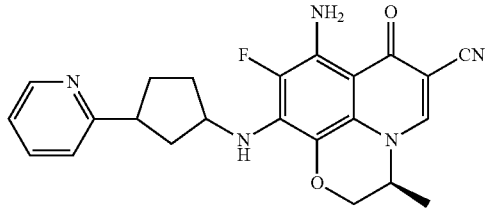

A mixture of (3S)-8-amino-9,10-difluoro-2,3-dihydro-3-methyl-7-oxo-7H-pyrido[1,2,3-de][1,4]benzoxazine-6-carbonitrile (180 mg, 0.649 mmol), cis-3-(2-pyridyl)cyclopentylamine (158 mg, 0.973 mmol) and triethylamine (0.200 mL, 0.976 mmol) in anhydrous DMSO (3 mL) was stirred at 80° C. for 8 h. After cooling, the reaction mixture was poured into ice-water and then extracted with $CH_2Cl_2$-MeOH. The organic layer was washed with water and brine, and dried over anhyd $Na_2SO_4$ followed by the removal of solvent. The crude product was purified by column chromatography (Hexane/EtOAc=1/3) to yield (3S)-8-amino-9-fluoro-2,3-dihydro-3-methyl-7-oxo-10-[cis-3-(2-pyridyl)cyclopentylamino]-7H-pyrido[1,2,3-de][1,4]benzoxazine-6-carbonitrile (diastereomer mixture, 55.6 mg, 20%) as a yellow powder.

$^1$H-NMR (DMSO-$d_6$, 400 MHz) δ 1.34 (3H×½, d, J=6.7 Hz), 1.37 (3H×½, d, J=6.7 Hz), 1.65-1.93 (5H, m), 2.03-2.12 (1H, m), 2.27-2.37 (2H, m), 3.34-3.40 (1H, m), 3.99-4.10 (1H, m), 4.36 (1H, dd J=11.6. 3.7 Hz), 4.40-4.49 (2H, m), 6.56 (1H×½, d, J=7.3 Hz), 6.70 (1H×½, d, J=7.3 Hz), 6.93 (2H, brs), 7.22 (1H, t, J=6.1 Hz), 7.30 (1H, d, J=7.3 Hz), 7.70 (1H, t, J=7.3 Hz), 8.45 (1H, s), 8.55 (1H, t, J=5.5 Hz).

ESIMS (+) 420[M+H]$^+$.

HRESIMS (+) 420.18374 (Calcd for $C_{23}H_{23}FN_5O_2$, 420.18358).

Example 4

(3S)-8-amino-9-fluoro-2,3-dihydro-3-methyl-7-oxo-10-[trans-3-(1H-pyrazol-1-yl)cyclopentylamino]-7H-pyrido[1,2,3-de][1,4]benzoxazine-6-carbonitrile (F)

Step 1: 3-(1H-pyrazol-1-yl)cyclopentan-1-one

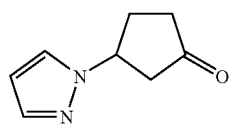

A mixture of pyrazole (6.85 g, 100 mmol), 2-cyclopenten-1-one (19.3 g, 235 mmol) and $ScCl_3$ (1.42 g, 9.38 mmol) in anhydrous $CH_2Cl_2$ (3 mL) was stirred at room temperature for 30 min. The reaction mixture was poured into water and then extracted with $CH_2Cl_2$. The organic layer was washed with brine, and dried over anhyd $Na_2SO_4$ followed by the removal of solvent. The crude product was purified by column chromatography (Hexane/EtOAc=4/1) to yield 3-(1H-pyrazol-1-yl)cyclopentan-1-one (14.1 g, 94%) as yellow oil.

$^1$H-NMR (CDCl$_3$-d, 400 MHz) δ 2.27-2.38 (1H, m), 2.39-2.67 (3H, m), 2.75 (1H, dd, J=18.3, 7.3 Hz), 2.84 (1H, dd, J=18.3, 7.3 Hz), 4.97 (1H, qui, J=6.1 Hz), 6.28 (1H, t, J=7.9, 1.8 Hz), 7.45 (1H, d, J=1.8 Hz), 7.54 (1H, s).

Step 2: cis-3-(1H-pyrazol-1-yl)cyclopentanol

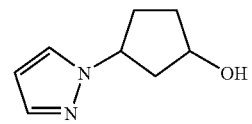

To a solution of 3-(1H-pyrazol-1-yl)cyclopentan-1-one (14.09 g, 93.8 mmol) in MeOH (150 ml) was added portionwise $NaBH_4$ (1.77 g. 46.8 mmol) at 0° C., and stirred for 30 min at room temperature. The reaction mixture was poured into 0.5M HCl and basified with sat. $NaHCO_3$ aq. and then extracted with $CH_2Cl_2$. The organic layer was dried over anhyd $Na_2SO_4$ followed by the removal of solvent. The crude product was purified by column chromatography (Hexane/EtOAc=2/1→1/1) to yield cis-3-(1H-pyrazol-1-yl)cyclopentanol (10.41 g, 73%) as colorless oil.

$^1$H-NMR (CDCl$_3$-d, 400 MHz) δ 1.80-1.91 (1H, m), 1.96-2.19 (3H, m), 2.19-2.33 (2H, m), 4.35-4.42 (1H, m), 4.80 (1H, td, J=7.9, 4.3 Hz), 5.75 (1H, d, J=9.8 Hz), 6.20 (1H, t, J=1.8 Hz), 7.43 (1H, d, J=1.8 Hz), 7.51 (1H, s).

EIMS (+) 219 [M]$^+$.

Step 3: trans-N-[3-(1H-pyrazol-1-yl)cyclopentyl]phthalimide

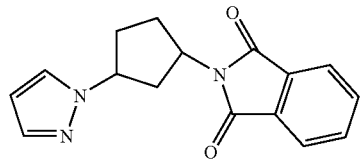

A solution of cis-3-(1H-pyrazol-1-yl)cyclopentanol (5.01 g, 32.9 mmol) in THF (150 mL) was cooled to 0° C. and treated with phthalimide (5.33 g, 36.2 mmol), diisopropylazodicarboxylate (7.1 mL, 36.1 mmol) and triphenylphosphine (9.48 g, 36.1 mmol). The reaction mixture was stirred at 0° C. for 4 h. The reaction mixture was poured water and then extracted with EtOAc. The organic layer was dried over anhyd $Na_2SO_4$ followed by the removal of solvent. The crude product was purified by column chromatography (Chromatrex, Hexane/EtOAc=5/1) to yield trans-N-[3-(1H-pyrazol-1-yl)cyclopentyl]phthalimide (4.85 g, 52%) as a colorless powder.

$^1$H-NMR (CDCl$_3$-d, 400 MHz) δ 2.16-2.33 (3H, m), 2.45-2.56 (2H, m), 2.56-2.65 (1H, m), 5.00-5.10 (1H, m), 5.16 (1H, qui, J=7.3 Hz), 6.25 (1H, t, J=1.8 Hz), 7.47 (1H, d, J=1.8 Hz), 7.55 (1H, d, J=1.8 Hz), 7.72 (2H, dd, J=5.5, 3.1 Hz), 7.84 (2H, dd, J=5.5, 3.1 Hz).

Step 4: trans-N-[3-(1H-pyrazol-1-yl)cyclopentyl]phthalimide (F) and trans-N-[3-(1H-pyrazol-1-yl)cyclopentyl]phthalimide (R)

trans-N-[3-(1H-pyrazol-1-yl)cyclopentyl]phthalimide (3.12 g) was separated by preparative HPLC using a Chiralpak IA column (φ20×250 mm) and MeCN as the eluent at a flow rate 5 mL/min for 1 h. The UV detector was set at 300 nm, the injection loop volume was 5 mL, and the injection load was 80 mg in a MeCN solution.

trans-N-[3-(1H-pyrazol-1-yl)cyclopentyl]phthalimide (F); 1.56 g, >99% purify with >99% e.e. (Chiralpak IA column (φ4.6×250 mm), MeCN, 0.5 mL/min, Rt=10.3 min)

trans-N-[3-(1H-pyrazol-1-yl)cyclopentyl]phthalimide (R); 1.5 g, >99% purify with >99% e.e. (Chiralpak IA column (φ4.6×250 mm), MeCN, 0.5 mL/min, Rt=15.2 min)

Step 5: trans-3-(1H-pyrazol-1-yl)cyclopentylamine (F)

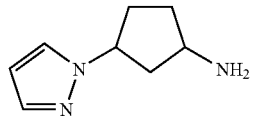

A mixture of trans-N-[3-(1H-pyrazol-1-yl)cyclopentyl]phthalimide (F) (1.53 g, 5.44 mmol), and hydrazinemonohydorate (0.53 mL, 10.9 mmol) in EtOH (30 mL) was stirred at reflux for 4 h. After cooling, the reaction mixture was filtered followed by the removal of solvent. The crude product was purified by column chromatography (Chromatrex, $CH_2Cl_2$/EtOH=30/1) to yield trans-3-(1H-pyrazol-1-yl)cyclopentylamine (427 mg, 52%) as yellow oil.

$^1$H-NMR ($CDCl_3$-d, 400 MHz) δ 1.30-1.50 (3H, m), 1.88-1.98 (1H, m), 2.01-2.10 (1H, m), 2.15-2.25 (1H, m), 2.27-2.42 (2H, m), 3.74 (1H, qui, J=6.1 Hz), 4.88 (1H, qui, J=7.3 Hz), 6.22 (1H, d, J=1.8 Hz), 7.40 (1H, d, J=1.8 Hz), 7.51 (1H, s).

Step 6: (3S)-8-amino-9-fluoro-2,3-dihydro-3-methyl-7-oxo-10-[trans-3-(1H-pyrazol-1-yl)cyclopentylamino]-7H-pyrido[1,2,3-de][1,4]benzoxazine-6-carbonitrile (F)

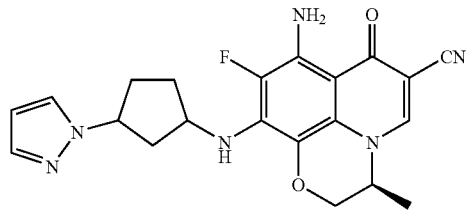

A mixture of (3S)-8-amino-9,10-difluoro-2,3-dihydro-3-methyl-7-oxo-7H-pyrido[1,2,3-de][1,4]benzoxazine-6-carbonitrile (580 mg, 2.09 mmol), trans-3-(1H-pyrazol-1-yl)cyclopentylamine (380 mg, 2.51 mmol) and di-isopropylethylamine (0.80 mL, 4.59 mmol) in anhydrous DMSO (12 mL) was stirred at 100° C. for 7 h. After cooling, the reaction mixture was poured into ice-water and then extracted with $CH_2Cl_2$-MeOH. The organic layer was washed with water and brine, and dried over anhyd $Na_2SO_4$ followed by the removal of solvent. The crude product was purified by column chromatography (EtOAc) to yield (3S)-8-amino-9-fluoro-2,3-dihydro-3-methyl-7-oxo-10-[trans-3-(1H-pyrazol-1-yl)cyclopentylamino]-7H-pyrido[1,2,3-de][1,4]benzoxazine-6-carbonitrile (125 mg, 15%) as a yellow powder.

$^1$H-NMR (DMSO-$d_6$, 400 MHz) δ 1.35 (3H, d, J=6.7 Hz), 1.60-1.73 (1H, m), 1.86-1.98 (1H, m), 2.11-2.29 (4H, m), 4.04 (1H, d, J=10.3 Hz), 4.31 (1H, d, J=10.3 Hz), 4.44 (1H, q, J=6.7 Hz), 4.55 (1H, q, J=6.7 Hz), 4.89 (1H, qui, J=6.7 Hz), 5.31 (1H, d, J=8.5 Hz), 6.20 (1H, t, J=1.8 Hz), 6.95 (2H, brs), 7.43 (1H, s), 7.74 (1H, d, J=1.8 Hz), 8.46 (1H, s).
ESIMS (+) 409 [M+H]$^+$.

HRESIMS (+) 409.17920 (Calcd for $C_{21}H_{22}FN_6O_2$, 409.17883).
anal. C, 61.70%; H, 5.17%; N, 20.25%. Calcd for $C_{21}H_{21}FN_6O_2$, 0.1$H_2O$, C, 61.48%; H, 5.21%; N, 20.49%.

Example 5

(3S)-8-amino-9-fluoro-2,3-dihydro-3-methyl-7-oxo-10-[trans-3-(1H-pyrazol-1-yl)cyclopentylamino]-7H-pyrido[1,2,3-de][1,4]benzoxazine-6-carbonitrile (R)

Step 1: trans-3-(1H-pyrazol-1-yl)cyclopentylamine (R)

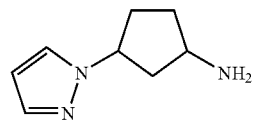

A mixture of trans-N-[3-(1H-pyrazol-1-yl)cyclopentyl]phthalimide (R) (1.49 g, 5.30 mmol), and hydrazinemonohydorate (0.51 mL, 10.5 mmol) in EtOH (30 mL) was stirred at reflux for 3 h. After cooling, the reaction mixture was filtered followed by the removal of solvent. The crude product was purified by column chromatography (Chromatrex, $CH_2Cl_2$/EtOH=30/1) to yield trans-3-(1H-pyrazol-1-yl)cyclopentylamine (517 mg, 65%) as yellow oil.

$^1$H-NMR ($CDCl_3$-d, 400 MHz) δ 1.30-1.50 (3H, m), 1.88-1.98 (1H, m), 2.01-2.10 (1H, m), 2.15-2.25 (1H, m), 2.27-2.42 (2H, m), 3.74 (1H, qui, J=6.1 Hz), 4.88 (1H, qui, J=7.3 Hz), 6.22 (1H, d, J=1.8 Hz), 7.40 (1H, d, J=1.8 Hz), 7.51 (1H, s).
CIMS (+) 152 [M+H]$^+$.

Step 2: (3S)-8-amino-9-fluoro-2,3-dihydro-3-methyl-7-oxo-10-[trans-3-(1H-pyrazol-1-yl)cyclopentylamino]-7H-pyrido[1,2,3-de][1,4]benzoxazine-6-carbonitrile (R)

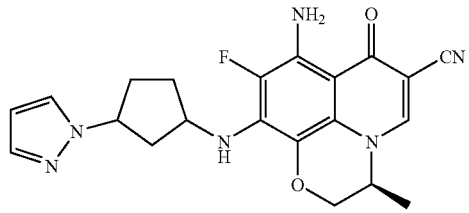

A mixture of (3S)-8-amino-9,10-difluoro-2,3-dihydro-3-methyl-7-oxo-7H-pyrido[1,2,3-de][1,4]benzoxazine-6-carbonitrile (702 mg, 2.53 mmol), trans-3-(1H-pyrazol-1-yl)cyclopentylamine (460 mg, 3.04 mmol) and di-isopropylethylamine (0.970 mL, 5.57 mmol) in anhydrous DMSO (14 mL) was stirred at 100° C. for 7 h. After cooling, the reaction mixture was poured into ice-water and then extracted with $CH_2Cl_2$-MeOH. The organic layer was washed with water and brine, and dried over anhyd $Na_2SO_4$ followed by the removal of solvent. The crude product was purified by column chromatography (Hexane/EtOAc=1/10→EtOAc) to yield (3S)-8-amino-9-fluoro-2,3-dihydro-3-methyl-7-oxo-10-[trans-3-(1H-pyrazol-1-yl)cyclopentylamino]-7H-pyrido[1,2,3-de][1,4]benzoxazine-6-carbonitrile (108 mg, 10%) as a yellow powder.

¹H-NMR (DMSO-d₆, 400 MHz) δ 1.35 (3H, d, J=6.7 Hz), 1.63-1.75 (1H, m), 1.86-1.98 (1H, m), 2.07-2.30 (4H, m), 4.05 (1H, d, J=11.5 Hz), 4.31 (1H, d, J=10.9 Hz), 4.44 (1H, q, J=6.7 Hz), 4.54 (1H, q, J=6.7 Hz), 4.89 (1H, qui, J=6.7 Hz), 5.30 (1H, d, J=8.5 Hz), 6.20 (1H, t, J=1.8 Hz), 6.94 (2H, brs), 7.42 (1H, s), 7.74 (1H, d, J=1.8 Hz), 8.46 (1H, s).

ESIMS (+) 409 [M+H]⁺.

HRESIMS (+) 409.17826 (Calcd for $C_{21}H_{22}FN_6O_2$, 409.17883).

anal. C, 61.16%; H, 5.08%; N, 20.06%. Calcd for $C_{21}H_{21}FN_6O_2$, 0.3H₂O, C, 60.95%; H, 5.26%; N, 20.31%.

Example 6

(3S)-8-amino-9-fluoro-2,3-dihydro-3-methyl-7-oxo-10-[cis-4-(3-pyridyl)cyclohexylamino]-7H-pyrido[1,2,3-de][1,4]benzoxazine-6-carbonitrile Step 1: 4-hydroxy-4-(3-pyridyl)cyclohexanone ethylene acetal

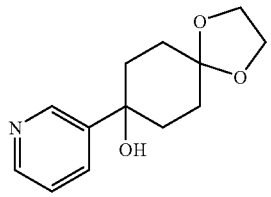

To a solution of n-BuLi (1.59 M in Hexane, 45 mL. 71.6 mmol) in dry ether (150 mL) was added a solution of 3-Bromopyridine (11.24 g, 71.1 mmol) in dry ether (70 mL) dropwise at −78° C. After stirring for 10 min, a solution of cyclohexane-1,4-dione monoetylene acetal (9.25 g, 59.2 mmol) in THF (70 mL) was added over a period of 20 min at −78° C., and stirred for 3 h. To the reaction mixture was added with water. The aqueous layer was extracted with CH₂Cl₂, and the organic layer was washed with brine. The extracts were combined with the organic layer. After drying and concentration, the crude product was purified by column chromatography (Hexane/EtOAc=2/1) to yield 4-hydroxy-4-(3-pyridyl)cyclohexanone ethylene acetal (6.55 g, 47%) as a pale yellow powder.

¹H-NMR (CDCl₃-d, 400 MHz) δ 1.65-1.78 (3H, m), 1.84 (2H, d, J=11.6 Hz), 2.05-2.23 (4H, m), 3.96-4.05 (4H, m), 7.27 (1H, dd, J=7.9, 4.8 Hz), 7.84 (1H, dt, J=7.9, 1.2 Hz), 8.49 (1H, dd, J=4.9. 1.2 Hz), 8.78 (1H, d, J=1.2 Hz). EIMS (+) 235 [M]⁺.

Step 2: 4-(3-pyridyl)cyclohex-3-en-1-one ethylene acetal

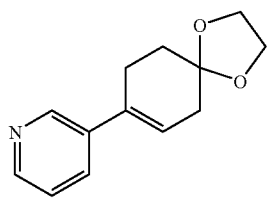

Thionyl chloride (10 mL) was added to a solution of 4-hydroxy-4-(3-pyridyl)cyclohexanone ethylene acetal (6.53 g, 27.8 mmol) in pyridine (60 mL) at −10° C. After stirring 0° C. for 30 min, the reaction mixture was poured onto ice. The aqueous layer was adjusted to pH 8 with 2M NaOH aq., and extracted with CH₂Cl₂, After drying and concentration, the crude product was purified by column chromatography (Hexane/EtOAc=2/1) to yield 4-(3-pyridyl)cyclohex-3-en-1-one ethylene acetal (4.85 g, 62%) as colorless oil.

¹H-NMR (CDCl₃-d, 400 MHz) δ 1.94 (2H, d, J=6.7 Hz), 2.47-2.51 (2H, m), 2.64-2.70 (2H, m), 4.03 (4H, s), 6.03-6.07 (1H, m), 7.23 (1H, dd, J=7.9, 5.5 Hz), 7.67 (1H, dt, J=7.9, 1.8 Hz), 8.46 (1H, dd, J=4.9. 1.8 Hz), 8.66 (1H, d, J=1.8 Hz).

Step 3: 4-(3-pyridyl)cyclohexanone ethylene acetal

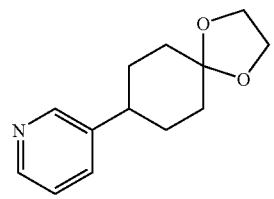

A mixture of 4-(3-pyridyl)cyclohex-3-en-1-one ethylene acetal (4.80 g, 22.1 mmol) in EtOAc (50 mL) containing 10% Pd/C (458 mg) was hydrogenated under atmospheric pressure for 3 h. After filtration of the catalyst, the solution was concentrated in vacuo, to yield 4-(3-pyridyl)cyclohexanone ethylene acetal (4.81 g, 99%) as yellow solid.

¹H-NMR (CDCl₃-d, 400 MHz) δ 1.66-1.76 (6H, m), 1.80 (2H, d, J=11.6 Hz), 1.88 (4H, d, J=11.0 Hz), 2.60 (1H, t, J=11.0 Hz), 3.99 (4H, s), 7.22 (1H, dd, J=7.9, 4.9 Hz), 7.56 (1H, d, J=7.9 Hz), 8.44 (1H, d, J=4.9 Hz), 8.50 (1H, d, J=1.2 Hz).

EIMS (+) 219 [M]⁺.

Step 4: 4-(3-pyridyl)cyclohexanone

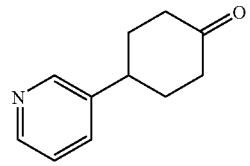

Water (1 mL) was added to a cod solution of 4-(3-pyridyl)cyclohexanone ethylene acetal (4.79 g, 21.9 mmol) in CF₃CO₂H (20 mL). After stirring room temperature for 6 h, the reaction mixture was added dropwise to sat. NaHCO₃. aq. The resulting mixture was adjusted to pH 8 with 2M NaOH aq. and extracted with CH₂Cl₂, After drying and consentration, the crude product was purified by column chromatography (Hexane/EtOAc=1/1→0/1) to yield 4-(3-pyridyl)cyclohexanone (3.23 g, 84%) as a colorless powder.

¹H-NMR (CDCl₃-d, 400 MHz) δ 1.90-2.04 (2H, m), 2.22-2.30 (2H, m), 2.47-2.61 (4H, m), 3.07 (1H, tt, J=12.2, 3.1 Hz), 7.23-7.30 (1H, m), 7.55 (1H, d, J=7.9 Hz), 8.50 (1H, dd, J=4.9, 1.2 Hz), 8.55 (1H, d, J=1.2 Hz).

EIMS (+) 175 [M]⁺.

Step 5: trans-4-(3-pyridyl)cyclohexanol

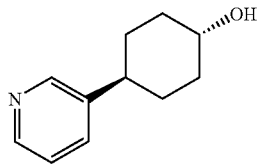

To a solution of 4-(3-pyridyl)cyclohexanone (3.22 g, 18.4 mmol) in MeOH (25 ml) was added portionwise NaBH₄ (348 mg. 9.30 mmol) at 0° C., and stirred for 30 min at room temperature. The reaction mixture was poured into 0.5M HCl and basified with sat. NaHCO₃ aq. and then extracted with CH₂Cl₂. The organic layer was dried over anhyd Na₂SO₄ followed by the removal of solvent. The crude product was purified by column chromatography (Hexane/EtOAc=5/1) to yield trans-4-(3-pyridyl)cyclohexanol (2.48 g, 76%) as a colorless powder.

$^1$H-NMR (CDCl$_3$-d, 400 MHz) δ 1.38-1.61 (4H, m), 1.90-1.98 (2H, m), 2.09-2.16 (2H, m), 2.53 (1H, tt, J=11.6, 3.7 Hz), 3.65-3.76 (1H, m), 7.22 (1H, dd, J=7.9, 4.9 Hz), 7.51 (1H, dt, J=7.9, 1.8 Hz), 8.44 (1H, dd, J=4.9, 1.8 Hz), 8.48 (1H, d, J=1.8 Hz).

CIMS (+) 178 [M+H]$_+$.

Step 6: cis-N-[4-(3-pyridiyl)cyclohexyl]phthalimide

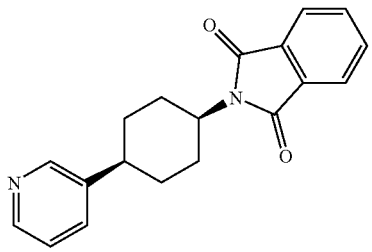

A solution of trans-4-(3-pyridyl)cyclohexanol (1.38 g, 7.79 mmol) in THF (70 mL) was cooled to 0° C. and treated with phthalimide (1.26 g, 8.58 mmol), diisopropylazodicarboxylate (1.7 mL, 8.63 mmol) and triphenylphosphine (1.26 g, 8.56 mmol). The reaction mixture was stirred at room temperature for 6 h. The reaction mixture was poured water and then extracted with EtOAc. The organic layer was dried over anhyd Na₂SO₄ followed by the removal of solvent. The crude product was purified by column chromatography (Hexane/EtOAc=3/1→2/1) to yield cis-N-[4-(3-pyridiyl)cyclohexyl]phthalimide (1.54 g, 64%) as a colorless powder.

$^1$H-NMR (CDCl$_3$-d, 400 MHz) δ 1.65-1.75 (2H, m), 1.90-2.03 (2H, m), 2.26-2.48 (4H, m), 3.10-3.18 (1H, m), 4.25-4.35 (1H, m), 7.30 (1H, dd, J=7.9, 4.9 Hz), 7.69 (2H, dd, J=5.5, 3.0 Hz), 7.80 (2H, dd, J=5.5, 3.0 Hz), 7.84 (1H, d, J=7.9 Hz), 8.47 (1H, d, J=4.9 Hz), 8.66 (1H, s).

EIMS (+) 306 [M]$_+$.

Step 7: cis-4-(3-pyridiyl)cyclohexylamine

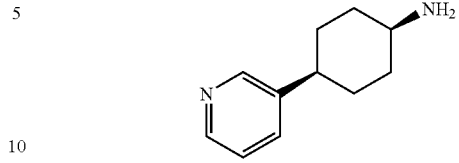

A solution of cis-N-[4-(3-pyridiyl)cyclohexyl]phthalimide (1.37 g, 4.47 mmol), and hydrazinemonohydorate (0.45 mL, 9.00 mmol) in EtOH (30 mL) was stirred at reflux for 3 h. After cooling, the reaction mixture was filtered followed by the removal of solvent. The crude product was purified by column chromatography (Chromatrex, CH₂Cl₂/EtOH=20/1) to yield cis-4-(3-pyridiyl)cyclohexylamine (705 mg, 89%) as yellow oil.

$^1$H-NMR (CDCl$_3$-d, 400 MHz) δ 1.48 (2H, brs), 1.64-1.80 (6H, m), 1.83-1.95 (2H, m), 2.55-2.65 (1H, m), 3.23-3.30 (1H, m), 7.22 (1H, dd, J=7.9, 4.9 Hz), 7.57 (1H, d, J=7.9 Hz), 8.43 (1H, dd, J=4.8, 1.8 Hz), 8.51 (1H, d, J=1.8 Hz).

EIMS (+) 176 [M]$^+$.

Step 8: (3S)-8-amino-9-fluoro-2,3-dihydro-3-methyl-7-oxo-10-[cis-4-(3-pyridyl)cyclohexylamino]-7H-pyrido[1,2,3-de][1,4]benzoxazine-6-carbonitrile

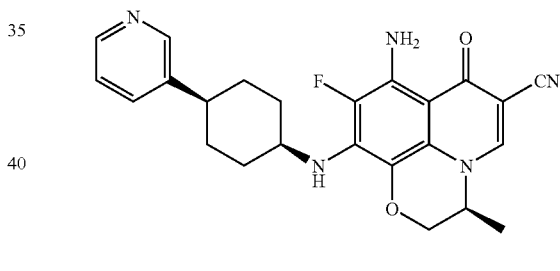

A mixture of (3S)-8-amino-9,10-difluoro-2,3-dihydro-3-methyl-7-oxo-7H-pyrido[1,2,3-de][1,4]benzoxazine-6-carbonitrile (792 mg, 2.86 mmol), cis-4-(3-pyridiyl)cyclohexylamine (605 mg, 3.43 mmol) and diisopropylethylamine (1.0 mL, 5.74 mmol) in anhydrous DMSO (14 mL) was stirred at 100° C. for 8 h. After cooling, the reaction mixture was poured into ice-water and then extracted with CH₂Cl₂-MeOH. The organic layer was washed with water and brine, and dried over anhyd Na₂SO₄ followed by the removal of solvent. The crude product was purified by column chromatography (EtOAc) to yield (3S)-8-amino-9-fluoro-2,3-dihydro-3-methyl-7-oxo-10-[cis-4-(3-pyridyl)cyclohexylamino]-7H-pyrido[1,2,3-de][1,4]benzoxazine-6-carbonitrile (152 mg, 12%) as a yellow powder.

$^1$H-NMR (DMSO-d$_6$, 400 MHz) δ 1.36 (3H, d, J=6.7 Hz), 1.59-1.89 (8H, m), 2.62-2.71 (1H, m), 4.01-4.13 (2H, m), 4.40 (1H, d, J=11.5 Hz), 4.44-4.51 (1H, m), 4.92 (1H, d, J=8.5 Hz), 6.97 (2H, brs), 7.33 (1H, dd, J=7.9, 4.8 Hz), 7.66 (1H, d, J=7.9 Hz), 8.40 (1H, dd, J=4.2, 1.8 Hz), 8.47-8.50 (2H, m).

ESIMS (+) 434 [M+H]$^+$.

HRESIMS (+) 434.20011 (Calcd for C$_{24}$H$_{25}$FN$_5$O$_2$, 434.19923).

Anal. C, 66.38%; H, 5.58%; N, 15.88%. Calcd for $C_{24}H_{24}FN_5O_2$, C, 66.50%; H, 5.58%; N, 16.16%.

Example 7

(3S)-8-amino-9-fluoro-2,3-dihydro-3-methyl-7-oxo-10-[trans-4-(3-pyridyl)cyclohexylamino]-7H-pyrido[1,2,3-de][1,4]benzoxazine-6-carbonitrile

Step 1: cis-4-(3-pyridyl)cyclohexanol

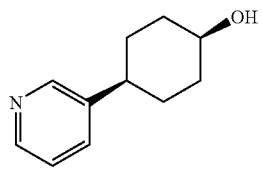

To a solution of 4-(3-pyridyl)cyclohexanone (3.22 g, 18.4 mmol) in MeOH (25 ml) was added portionwise NaBH$_4$ (348 mg. 9.30 mmol) at 0° C., and stirred for 30 min at room temperature. The reaction mixture was poured into 0.5M HCl and basified with sat. NaHCO$_3$ aq. and then extracted with CH$_2$Cl$_2$. The organic layer was dried over anhyd Na$_2$SO$_4$ followed by the removal of solvent. The crude product was purified by column chromatography (Hexane/EtOAc=5/1) to yield cis-4-(3-pyridyl)cyclohexanol (510 mg, 16%) as a colorless powder.

$^1$H-NMR (CDCl$_3$-d, 400 MHz) δ 1.63-1.76 (5H, m), 1.86-1.98 (4H, m), 2.52-2.62 (1H, m), 4.13-4.18 (1H, m), 7.23 (1H, dd, J=7.9, 4.3 Hz), 7.56 (1H, dt, J=7.9, 1.8 Hz), 8.44 (1H, dd, J=4.9, 1.8 Hz), 8.50 (1H, d, J=2.4 Hz).

CIMS (+) 178 [M+H]$^+$.

Step 2: cis-4-(3-pyridyl)cyclohexane methanesulfanate

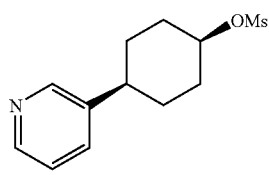

A mixture of cis-4-(3-pyridyl)cyclohexanol (302 mg, 1.70 mmol), methanesulfonyl chloride (0.290 mL, 3.76 mmol) and triethylamine (1.0 mL, 3.66 mmol) in anhydrous CH$_2$Cl$_2$ (15 mL) was stirred at room temperature for 2.5 h. The reaction mixture was poured into ice-water and basified with sat. NaHCO$_3$ aq. and then extracted with CH$_2$Cl$_2$. The organic layer was dried over anhyd Na$_2$SO$_4$ followed by the removal of solvent. The crude product was purified by column chromatography (Hexane/EtOAc=1/2) to yield cis-4-(3-pyridyl)cyclohexane methanesulfanate (423 mg, 97%) as a colorless powder.

$^1$H-NMR (CDCl$_3$-d, 400 MHz) δ 1.73-1.95 (6H, m), 2.25 (2H, d, J=14.5 Hz), 2.58-2.68 (1H, m), 3.06 (3H, s), 5.05-5.12 (1H, m), 7.20-7.28 (1H, m), 7.55 (1H, d, J=7.9 Hz), 8.46 (1H, dd, J=4.8, 1.2 Hz), 8.49 (1H, d, J=1.2 Hz).

EIMS (+) 255 [M]$^+$.

Step 3: trans-4-(3-pyridyl)cyclohexylazide

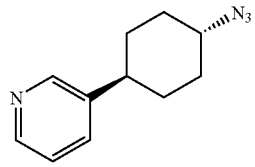

A mixture of cis-4-(3-pyridyl)cyclohexane methanesulfanate (407 mg, 1.59 mmol), sodium azide (507 mg, 7.80 mmol) in anhydrous DMF (8 mL) was stirred at 60° C. for 4.5 h. The reaction mixture was poured into ice-water and then extracted with CH$_2$Cl$_2$. The organic layer was dried over anhyd Na$_2$SO$_4$ followed by the removal of solvent. The crude product was purified by column chromatography (Hexane/EtOAc=2/1) to yield trans-4-(3-pyridyl)cyclohexylazide (245 mg, 76%) as colorless oil.

$^1$H-NMR (CDCl$_3$-d, 400 MHz) δ 1.45-1.63 (4H, m), 1.95-2.06 (2H, m), 2.10-2.21 (2H, m), 2.50-2.61 (1H, m), 3.32-3.42 (1H, m), 7.22 (1H, dd J=7.9, 4.8 Hz), 7.49 (1H, d, J=7.9 Hz), 8.46 (1H, dd, J=4.8, 1.8 Hz), 8.47 (1H, d, J=1.8 Hz).

CIMS (+) 203 [M+H]

Step 4: trans-4-(3-pyridiyl)cyclohexylamine

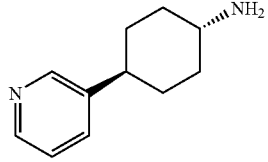

A solution of trans-4-(3-pyridyl)cyclohexylazide (238 mg, 1.18 mmol) in EtOH (20 mL) was treated with hydrogen under atmospheric pressure over 10% Pd/C (21.2 mg) for 2 h. The catalyst was removed by filtration through Celite and the filtrate was concentrated in vacuo and dried to yield trans-4-(3-pyridiyl)cyclohexylamine (202 mg, 97%) as yellow oil.

$^1$H-NMR (CDCl$_3$-d, 400 MHz) δ 1.20-1.33 (2H, m), 1.87-2.04 (4H, m), 2.51 (1H, tt, J=12.1, 3.0 Hz), 2.75 (1H, tt, J=11.5, 3.0 Hz), 7.21 (1H, dd J=7.9, 4.8 Hz), 7.51 (1H, dd, J=7.9, 1.8 Hz), 8.44 (1H, dd, J=4.8, 1.2 Hz), 8.48 (1H, d, J=1.2 Hz).

EIMS (+) 176 [M]$^+$.

Step 5: (3S)-8-amino-9-fluoro-2,3-dihydro-3-methyl-7-oxo-10-[trans-4-(3-pyridyl)cyclohexylamino]-7H-pyrido[1,2,3-de][1,4]benzoxazine-6-carbonitrile

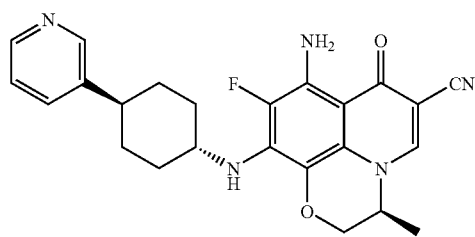

A mixture of (3S)-8-amino-9,10-difluoro-2,3-dihydro-3-methyl-7-oxo-7H-pyrido[1,2,3-de][1,4]benzoxazine-6-carbonitrile (290 mg, 1.05 mmol), trans-4-(3-pyridiyl)cyclohexylamine (220 mg, 1.25 mmol) and diisopropylethylamine (0.4 mL, 2.30 mmol) in anhydrous DMSO (4 mL) was stirred at 100° C. for 8 h. After cooling, the reaction mixture was poured into ice-water and then extracted with $CH_2Cl_2$-MeOH. The organic layer was washed with water and brine, and dried over anhyd $Na_2SO_4$ followed by the removal of solvent. The crude product was purified by column chromatography (EtOAc) to yield (3S)-8-amino-9-fluoro-2,3-dihydro-3-methyl-7-oxo-10-[trans-4-(3-pyridyl)cyclohexylamino]-7H-pyrido[1,2,3-de][1,4]benzoxazine-6-carbonitrile (33.2 mg, 7%) as a yellow powder.

$^1$H-NMR (DMSO-$d_6$, 400 MHz) δ 1.35 (3H, d, J=6.7 Hz), 1.42-1.48 (2H, m), 1.50-1.63 (2H, m), 1.80-1.88 (2H, m), 2.01-2.08 (2H, m), 3.70-3.82 (1H, m), 4.06 (1H, d, J=11.9 Hz), 4.33 (1H, d, J=11.9 Hz), 4.42-4.50 (1H, m), 4.96 (1H, J=7.9 Hz), 6.95 (2H, brs), 7.29 (1H, dd, J=7.3, 4.8 Hz), 7.68 (1H, d, J=7.9 Hz), 8.39 (1H, d, J=4.8 Hz), 8.45-8.50 (2H, m).

ESIMS (+) 434 [M+H]$^+$.

HRESIMS (+) 434.20016 (Calcd for $C_{24}H_{25}FN_5O_2$, 434.19923).

anal. C, 65.33%; H, 5.65%; N, 15.23%. Calcd for $C_{24}H_{24}FN_5O_2$, C, 66.50%; H, 5.58%; N, 16.16%.

Example 8

(3S)-8-amino-9-fluoro-2,3-dihydro-3-methyl-7-oxo-10-[(1S,3S)-3-(3-pyridyl)cyclopentylamino]-7H-pyrido[1,2,3-de][1,4]benzoxazine-6-carbonitrile Step 1: (1S,4S)-4-(3-pyridyl)-2-cyclopenten-1-ol

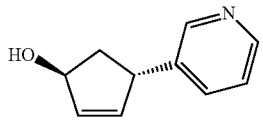

To a solution of 3-Iodopyridine (13.0 g, 63.3 mmol) in THF (30 mL) was added i-PrMgCl (38.0 mL, 76.0 mmol) at 3-9° C. After stirring was continued at room temperature for 30 min, CuCN (567 mg, 6.33 mmol) was added to the solution at 2° C. After stirring was continued at 3° C. for 30 min, to the resulting solution were added (1R,4S)-4-hydroxycyclopent-2-enyl acetate (3.00 g, 21.1 mmol) in THF (30 mL). The whole mixture was stirred at the room temperature for 2 h, and diluted with saturated $NH_4Cl$ with vigorous stirring. The products were extracted with EtOAc three times, and the combined layers were dried over $Na_2SO_4$. After concentration under reduced pressure, the residue was purified by column chromatography (NH, Hexane/EtOAc=4/1) to yield (1S,4S)-4-(3-pyridyl)-2-cyclopenten-1-ol (1.88 g, 55%) as yellow oil.

$^1$H-NMR (CDCl$_3$-d, 400 MHz) δ 1.81 (1H, brs), 2.04-2.14 (1H, m), 2.34 (1H, ddd, J=14.2, 8.1, 2.6 Hz), 4.14-4.20 (1H, m), 5.08 (1H, brs), 6.03 (1H, dd, J=5.5, 1.2 Hz), 6.07-6.12 (1H, m), 7.22 (1H, dd, J=8.3, 5.2 Hz), 7.42 (1H, dt, J=7.9, 1.8 Hz), 7.43 (1H, d, J=2.4 Hz), 8.46 (1H, dd, J=4.3, 1.2 Hz).

EIMS (+): 161.1 [M]$^+$.

Step 2: (1R,3R)-3-(3-pyridyl)cyclopentanol

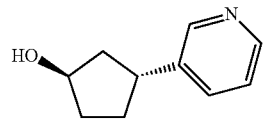

A mixture of (1S,4S)-4-(3-pyridyl)-2-cyclopenten-1-ol (1.86 g, 11.5 mmol) and 10% Pd/C (186 mg) in EtOH (35 mL) was stirred under hydrogen atmosphere for 3 h. The catalyst was removed by filtration over Celite and the filtrate was concentrated in vacuo. (1R,3R)-3-(3-pyridyl)cyclopentanol (1.82 g, 97%) was yield as yellow oil.

$^1$H-NMR (CDCl$_3$-d, 400 MHz) δ 1.56-1.88 (4H, m), 2.08-2.36 (4H, m), 3.37-3.49 (1H, m), 4.53-4.59 (1H, m), 7.24-7.30 (1H, m), 7.58 (1H, dt, J=7.9, 1.8 Hz), 8.46 (1H, d, J=4.3 Hz), 8.53 (1H, s).

CIMS (+): 164.1 [M+H]$^+$.

Step 3: (1S,3R)-3-(3-pyridyl)cyclopentyl acetate

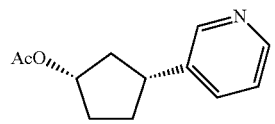

A solution of (1R,3R)-3-(3-pyridyl)cyclopentanol (3.47 g, 21.3 mmol) in THF (100 mL) was cooled to 4° C. and treated with acetic acid (1.34 mL, 23.4 mmol), Diisopropylazodicarboxylate (4.61 mL, 23.4 mmol) and triphenylphosphine (6.14 g, 23.4 mmol). The reaction mixture was stirred at room temperature for 12 h. The reaction mixture was diluted with EtOAc, and washed with $H_2O$ and brine. The organic layers was dried over $Na_2SO_4$. After concentration under reduced pressure, the residue was purified by column chromatography (NH, Hexane/EtOAc=6/1) to yield (1S,3R)-3-(3-pyridyl)cyclopentyl acetate (4.39 g, 100%) as colorless oil.

$^1$H-NMR (CDCl$_3$-d, 400 MHz) δ 1.70-2.18 (8H, m), 2.55-2.65 (1H, m), 3.03-3.15 (1H, m), 5.23-5.31 (1H, m), 7.24 (1H, dd, J=7.9, 4.9 Hz), 7.58 (1H, dt, J=7.9, 1.8 Hz), 8.46 (1H, dd, J=4.9, 1.8 Hz), 8.53 (1H, d, J=2.4 Hz).

CIMS (+): 206.1 [M+H]$^+$.

Step 4: (1S,3R)-3-(3-pyridyl)cyclopentanol

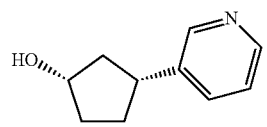

To a solution of (1S,3R)-3-(3-pyridyl)cyclopentyl acetate (5.43 g, 26.5 mmol) in MeOH (80 ml) was added 1N NaOH aq. (26 mL) at 4° C., and stirred for 2 h at same temperature. To the reaction mixture was added $H_2O$ and then extracted with $CH_2Cl_2$ four times, and the combined layers were dried over $Na_2SO_4$. After concentration under reduced pressure, the residue was purified by column chromatography (EtOAc) to yield (1S,3R)-3-(3-pyridyl)cyclopentanol (3.99 g, 92%) as colorless oil.

$^1$H-NMR (CDCl$_3$-d, 400 MHz) δ 1.60-2.18 (6H, m), 2.44-2.54 (1H, m), 3.02-3.13 (1H, m), 4.45-4.54 (1H, m), 7.23 (1H, dd, J=7.3, 4.9 Hz), 7.65 (1H, d, J=7.9 Hz), 8.43 (1H, dd, J=4.9, 1.2 Hz), 8.52 (1H, d, J=1.8 Hz).

CIMS (+): 164.1 [M+H]$^+$.

Step 5: (1R,3R)-N-[3-(3-pyridyl)cyclopentyl]phthalimide

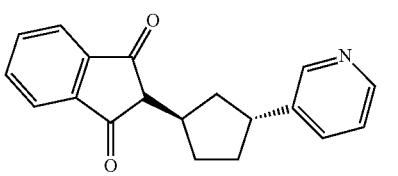

A solution of (1S,3R)-3-(3-pyridyl)cyclopentanol (3.95 g, 24.2 mmol) in THF (80 mL) was cooled to 4° C. and treated with phthalimide (3.91 g, 26.6 mmol), Diisopropylazodicarboxylate (5.24 mL, 26.6 mmol) and triphenylphosphine (6.98 g, 26.6 mmol). The reaction mixture was stirred at room temperature for 2 h. The reaction mixture was diluted with EtOAc, and washed with H$_2$O and brine. The organic layers was dried over Na$_2$SO$_4$. After concentration under reduced pressure, the residue was purified by column chromatography (Hexane/EtOAc=4/1) to yield (1R,3R)-N-[3-(3-pyridyl)cyclopentyl]phthalimide (6.27 g, 89%) as colorless powder.

$^1$H-NMR (CDCl$_3$-d, 400 MHz) δ 1.66-1.82 (1H, m), 2.09 (1H, dt, J=17.9, 6.7 Hz), 2.16-2.43 (3H, m), 2.45-2.56 (1H, m), 3.67-3.79 (1H, m), 4.87-4.99 (1H, m), 7.22-7.28 (1H, m), 7.59 (1H, d, J=7.3 Hz), 7.69-7.76 (2H, m), 7.81-7.89 (2H, m), 8.46 (1H, dd, J=4.9, 1.2 Hz), 8.56 (1H, d, J=1.8 Hz).

CIMS (+): 293.1 [M+H]$^+$.

Step 6: (1R,3R)-3-(3-pyridyl)cyclopentylamine

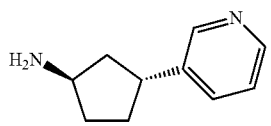

A mixture of (1R,3R)-N-[3-(3-pyridyl)cyclopentyl]phthalimide (3.00 g, 10.3 mmol) and hydrazinemonohydorate (1.00 mL, 20.5 mmol) in EtOH (40 mL) was stirred at room temperature for 1 h. The reaction mixture was filtered followed by the removal of solvent. The crude product was purified by column chromatography (NH, CHCl$_3$/MeOH=50/1) to yield (1R,3R)-3-(3-pyridyl)cyclopentylamine (1.63 g, 97%) as yellow oil.

$^1$H-NMR (CDCl$_3$-d, 400 MHz) δ 1.33-1.75 (4H, m), 1.81-1.95 (2H, m), 2.05-2.30 (2H, m), 3.29-3.41 (1H, m), 3.62-3.71 (1H, m), 7.21 (1H, dd, J=7.3, 4.9 Hz), 7.52 (1H, d, J=7.9 Hz), 8.43 (1H, dd, J=4.9, 1.2 Hz), 8.49 (1H, d, J=1.8 Hz).

CIMS (+): 163.1 [M+H]$^+$.

Step 7: (3S)-8-amino-9-fluoro-2,3-dihydro-3-methyl-7-oxo-10-[(1S,3S)-3-(3-pyridyl)cyclopentylamino]-7H-pyrido[1,2,3-de][1,4]benzoxazine-6-carbonitrile

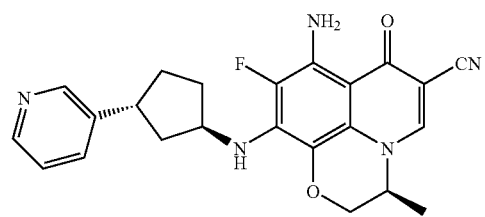

A mixture of (3S)-8-amino-9,10-difluoro-2,3-dihydro-3-methyl-7-oxo-7H-pyrido[1,2,3-de][1,4]benzoxazine-6-carbonitrile (1.00 g, 3.61 mmol), (1R,3R)-3-(3-pyridyl)cyclopentylamine (702 mg, 4.33 mmol) and diisopropylethylamine (1.38 mL, 7.94 mmol) in anhydrous DMSO (18 mL) was stirred at 91° C. for 7 h. After cooling, the reaction mixture was poured into ice-water and then extracted with CH$_2$Cl$_2$-MeOH. The organic layer was washed with water and brine, and dried over anhyd Na$_2$SO$_4$ followed by the removal of solvent. The crude product was purified by column chromatography (EtOAc) to yield (3S)-8-amino-9-fluoro-2,3-dihydro-3-methyl-7-oxo-10-[(1S,3S)-3-(3-pyridyl)cyclopentylamino]-7H-pyrido[1,2,3-de][1,4]benzoxazine-6-carbonitrile (247 mg, 16%) as a yellow powder.

$^1$H-NMR (DMSO-d$_6$, 400 MHz) δ 1.35 (3H, d, J=6.7 Hz), 1.54-1.80 (2H, m), 1.86-1.98 (1H, m), 2.02-2.29 (3H, m), 4.06 (1H, d, J=9.7 Hz), 4.33 (1H, d, J=10.3 Hz), 4.40-4.54 (2H, m), 5.23 (1H, d, J=6.1 Hz), 6.94 (2H, brs), 7.30 (1H, dd, J=7.9, 4.2 Hz), 7.67 (1H, d, J=7.9 Hz), 8.38 (1H, d, J=3.0 Hz), 8.43-8.50 (2H, m).

ESIMS (+): 420.2 [M+H]$^+$.

HRESIMS (+): 420.18332 (Calcd for C$_{23}$H$_{23}$FN$_5$O$_2$, 420.18358).

Example 9

(3S)-8-amino-9-fluoro-2,3-dihydro-3-methyl-7-oxo-10-[trans-3-(3-pyridyl)cyclohexylamino]-7H-pyrido[1,2,3-de][1,4]benzoxazine-6-carbonitrile Step 1: 3-(3-pyridyl)-2-cyclohexen-1-one

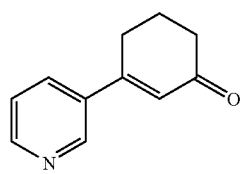

To a solution of n-BuLi (1.54 M in Hexane, 145 mL. 224 mmol) in Et$_2$O (600 ml) was added dropwise 3-Bromopyridine (22.0 mL, 224 mmol) at −75~−68° C., and stirred for 20 min. To a reaction mixture was added dropwise 3-ethoxy-2-cyclohexenone (25.0 mL, 187 mmol) at −75~−69° C., and stirred at room temperature for 1 h. The reaction mixture was acidified with 2M HCl (300 mL), and aqueous layer was washed with AcOEt. The aqueous layer was basified with 1M NaOH aq., and then extracted with CH$_2$Cl$_2$. The organic layer was washed with brine, and dried over anhyd Na$_2$SO$_4$ followed by the removal of solvent. The crude product was purified by column chromatography (Hexane/EtOAc=1/2) to yield 3-(3-pyridyl)-2-cyclohexen-1-one (21.5 g, 66%) as yellow powder.

$^1$H-NMR (CDCl$_3$-d, 400 MHz) δ 2.15-2.26 (2H, m), 2.52 (2H, t, J=6.7 Hz), 2.75-2.84 (2H, m), 6.43 (1H, s), 7.36 (1H, dd, J=7.9, 4.9 Hz), 7.82 (1H, dt, J=5.0, 2.6 Hz), 8.64 (1H, dd, J=4.9, 1.2 Hz), 8.80 (1H, d, J=1.8 Hz).

EIMS (+): 173.1 [M]$^+$.

Step 2: cis-3-(3-pyridyl)cyclohexanol

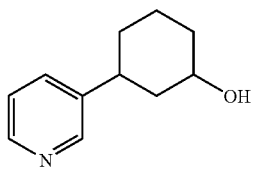

A mixture of 3-(3-pyridyl)-2-cyclohexen-1-one (19.1 g, 110 mmol) and 10% Pd/C (1.91 g) in EtOH (300 mL) was stirred under hydrogen atmosphere for 16 h. The catalyst was removed by filtration over Celite and the filtrate was concentrated in vacuo. To a solution of crude product in MeOH (360 ml) was added portionwise NaBH$_4$ (2.08 g. 55.0 mmol) at 3° C., and stirred for 30 min at same temperature. The reaction mixture was poured into ice-water and then extracted with AcOEt. The organic layer was dried over anhyd Na$_2$SO$_4$ followed by the removal of solvent. The crude product was purified by column chromatography (NH, Hexane/EtOAc=2/1) to yield cis-3-(3-pyridyl)cyclohexanol (14.6 g, 75%) as colorless oil.

$^1$H-NMR (CDCl$_3$-d, 400 MHz) δ 1.22-1.55 (4H, m), 1.79-1.99 (2H, m), 2.03-2.23 (2H, m), 2.62 (1H, tt, J=12.4, 3.2 Hz), 3.76 (1H, t, J=10.3 Hz), 7.23 (1H, dd, J=7.9, 4.8 Hz), 7.52 (1H, d, J=7.9 Hz), 8.42-8.52 (2H, m).

CIMS (+): 178.1 [M+H]$^+$.

Step 3: trans-N-[3-(3-pyridyl)cyclohexyl]phthalimide

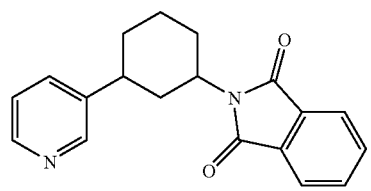

A solution of cis-3-(3-pyridyl)cyclohexanol (5.00 g, 28.2 mmol) in THF (100 mL) was cooled to 4° C. and treated with phthalimide (4.56 g, 31.0 mmol), Diisopropylazodicarboxylate (6.10 mL, 31.0 mmol) and triphenylphosphine (8.13 g, 31.0 mmol). The reaction mixture was stirred at room temperature for 2 h. The reaction mixture was diluted with EtOAc, and washed with H$_2$O and brine. The organic layers was dried over Na$_2$SO$_4$. After concentration under reduced pressure, the residue was purified by column chromatography (Hexane/EtOAc=4/1) to yield trans-N-[3-(3-pyridyl)cyclohexyl]phthalimide (5.18 g, 60%) as colorless powder.

$^1$H-NMR (CDCl$_3$-d, 400 MHz) δ 1.45-1.63 (1H, m), 1.74-1.86 (2H, m), 1.94 (1H, tt, J=13.3, 4.2 Hz), 2.16-2.28 (2H, m), 2.36 (1H, ddd, J=24.5, 12.4, 3.9 Hz), 2.72 (1H, td, J=12.7, 5.0 Hz), 3.43 (1H, brs), 4.39 (1H, tt, J=11.5, 3.8 Hz), 7.29 (1H, dd, J=7.9, 4.8 Hz), 7.67-7.88 (5H, m), 8.48 (1H, d, J=4.2 Hz), 8.67 (1H, d, J=1.8 Hz).

CIMS (+): 307.1 [M+H]$^+$.

Step 4: trans-3-(3-pyridyl)cyclohexylamine

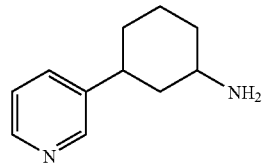

A mixture of trans-N-[3-(3-pyridyl)cyclohexyl]phthalimide (3.00 g, 9.79 mmol) and hydrazinemonohydorate (0.95 mL, 19.6 mmol) in EtOH (40 mL) was stirred at room temperature for 1.5 h. The reaction mixture was filtered followed by the removal of solvent. The crude product was purified by column chromatography (NH, EtOAc) to yield trans-3-(3-pyridyl)cyclohexylamine (1.08 g, 60%) as colorless oil.

$^1$H-NMR (CDCl$_3$-d, 400 MHz) δ 1.35-1.95 (10H, m), 2.95-3.07 (1H, m), 3.38 (1H, t, J=3.6 Hz), 7.21 (1H, dd, J=7.9, 4.8 Hz), 7.53 (1H, d, J=7.9 Hz), 8.43 (1H, dd, J=4.8, 1.2 Hz), 8.50 (1H, d, J=1.8 Hz).

CIMS (+): 177.1 [M+H]$^+$.

Step 5: (3S)-8-amino-9-fluoro-2,3-dihydro-3-methyl-7-oxo-10-[trans-3-(3-pyridyl)cyclohexylamino]-7H-pyrido[1,2,3-de][1,4]benzoxazine-6-carbonitrile

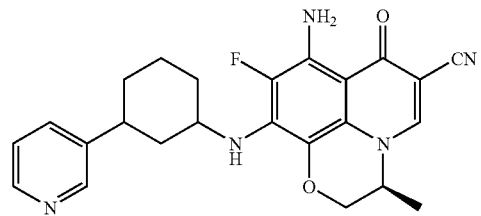

A mixture of (3S)-8-amino-9,10-difluoro-2,3-dihydro-3-methyl-7-oxo-7H-pyrido[1,2,3-de][1,4]benzoxazine-6-carbonitrile (800 mg, 2.89 mmol), trans-3-(3-pyridyl)cyclohexylamine (612 mg, 3.47 mmol) and diisopropylethylamine (1.11 mL, 6.36 mmol) in anhydrous DMSO (12 mL) was stirred at 84° C. for 9 h. After cooling, the reaction mixture was poured into ice-water and then extracted with CH$_2$Cl$_2$-MeOH. The organic layer was washed with water and brine, and dried over anhyd Na$_2$SO$_4$ followed by the removal of solvent. The crude product was purified by column chromatography (EtOAc) to yield (3S)-8-amino-9-fluoro-2,3-dihydro-3-methyl-7-oxo-10-[trans-3-(3-pyridyl)cyclohexylamino]-7H-pyrido[1,2,3-de][1,4]benzoxazine-6-carbonitrile (309 mg, 24%) as a yellow powder.

$^1$H-NMR (DMSO-d$_6$, 400 MHz) δ 1.37 (3H, dd, J=6.7, 4.3 Hz), 1.47-1.93 (8H, m), 2.80-2.95 (1H, m), 4.06-4.22 (2H, m), 4.35-4.52 (2H, m), 4.98 (1H, d, J=7.9 Hz), 6.95 (2H, brs), 7.29 (1H, dd, J=7.9, 4.8 Hz), 7.64 (1H, d, J=6.7 Hz), 8.38 (1H, dd, J=4.8, 1.2 Hz), 8.44 (1H, s), 8.49 (1H, s).

ESIMS (+): 434.2 [M+H]$^+$.

HRESIMS (+): 434.19998 (Calcd for $C_{24}H_{25}FN_5O_2$, 434.19923).

Example 10

(3S)-8-amino-9-fluoro-2,3-dihydro-3-methyl-7-oxo-10-[cis-3-(3-pyridyl)cyclohexylamino]-7H-pyrido[1,2,3-de][1,4]benzoxazine-6-carbonitrile

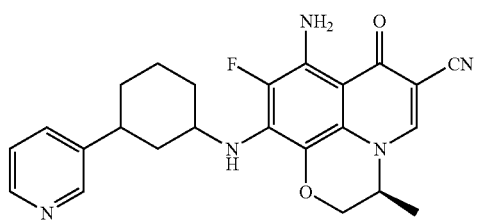

Step 1: trans-3-(3-pyridyl)cyclohexanol

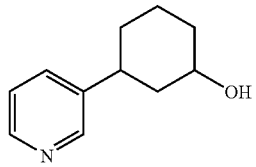

A mixture of 3-(3-pyridyl)-2-cyclohexen-1-one (19.1 g, 110 mmol) and 10% Pd/C (1.91 g) in EtOH (300 mL) was stirred under hydrogen atmosphere for 16 h. The catalyst was removed by filtration over Celite and the filtrate was concentrated in vacuo. To a solution of crude product in MeOH (360 ml) was added portionwise NaBH$_4$ (2.08 g. 55.0 mmol) at 3° C., and stirred for 30 min at same temperature. The reaction mixture was poured into ice-water and then extracted with AcOEt. The organic layer was dried over anhyd Na$_2$SO$_4$ followed by the removal of solvent. The crude product was purified by column chromatography (NH, Hexane/EtOAc=2/1) to yield trans-3-(3-pyridyl)cyclohexanol (4.19 g, 21%) as colorless powder.

$^1$H-NMR (CDCl$_3$-d, 400 MHz) δ 1.38-2.10 (8H, m), 3.00-3.15 (1H, m), 4.26 (1H, brs), 7.22 (1H, dd, J=7.9, 4.8 Hz), 7.52 (1H, d, J=7.9 Hz), 8.40-8.53 (2H, m).

CIMS (+): 178.1 [M+H]$^+$.

Step 2: cis-N-[3-(3-pyridyl)cyclohexyl]phthalimide

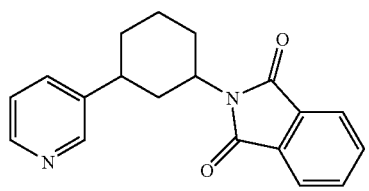

A solution of trans-3-(3-pyridyl)cyclohexanol (3.99 g, 22.5 mmol) in THF (90 mL) was cooled to 4° C. and treated with phthalimide (3.65 g, 24.8 mmol), Diisopropylazodicarboxylate (4.88 mL, 24.8 mmol) and triphenylphosphine (6.50 g, 24.8 mmol). The reaction mixture was stirred at room temperature for 30 min. The reaction mixture was diluted with EtOAc, and washed with H$_2$O and brine. The organic layers was dried over Na$_2$SO$_4$. After concentration under reduced pressure, the residue was purified by column chromatography (Hexane/EtOAc=4/1) to yield cis-N-[3-(3-pyridyl)cyclohexyl]phthalimide (1.66 g, 24%) as colorless powder.

$^1$H-NMR (CDCl$_3$-d, 400 MHz) δ 1.45-1.64 (2H, m), 1.79-1.98 (3H, m), 2.01-2.11 (1H, m), 2.24-2.38 (1H, m), 2.46 (1H, q, J=12.2 Hz), 2.68-2.79 (1H, m), 4.33 (1H, tt, J=12.2, 3.7 Hz), 7.23 (1H, dd, J=7.3, 4.9 Hz), 7.57 (1H, d, J=7.9 Hz), 7.67-7.75 (2H, m), 7.78-7.86 (2H, m), 8.45 (1H, dd, J=4.9, 1.2 Hz), 8.51 (1H, d, J=1.8 Hz).

EIMS (+): 306.1 [M]$^+$.

Step 3: cis-3-(3-pyridyl)cyclohexylamine

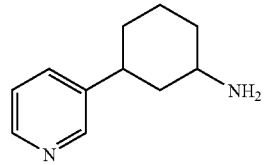

A mixture of cis-N-[3-(3-pyridyl)cyclohexyl]phtalimide (1.64 g, 5.35 mmol) and hydrazinemonohydorate (0.52 mL, 10.7 mmol) in EtOH (25 mL) was stirred at room temperature for 2 h. The reaction mixture was filtered followed by the removal of solvent. The crude product was purified by column chromatography (NH, EtOAc) to yield cis-3-(3-pyridyl)cyclohexylamine (348 g, 37%) as colorless oil.

$^1$H-NMR (CDCl$_3$-d, 400 MHz) δ 1.11 (1H, ddd, J=24.5, 12.4, 3.3 Hz), 1.20-1.70 (4H, m), 1.71-2.19 (5H, m), 2.62 (1H, tt, J=12.1, 3.3 Hz), 2.83 (1H, tt, J=11.2, 3.8 Hz), 7.22 (1H, dd, J=7.9, 4.8 Hz), 7.51 (1H, d, J=7.9 Hz), 8.40-8.91 (2H, m).

EIMS (+): 176.1 [M]$^+$.

Step 4: (3S)-8-amino-9-fluoro-2,3-dihydro-3-methyl-7-oxo-10-[cis-3-(3-pyridyl)cyclohexylamino]-7H-pyrido[1,2,3-de][1,4]benzoxazine-6-carbonitrile

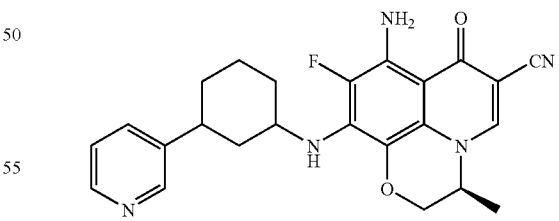

A mixture of (3S)-8-amino-9,10-difluoro-2,3-dihydro-3-methyl-7-oxo-7H-pyrido[1,2,3-de][1,4]benzoxazine-6-carbonitrile (457 mg, 1.65 mmol), cis-3-(3-pyridyl)cyclohexylamine (348 mg, 1.97 mmol) and diisopropylethylamine (0.63 mL, 3.63 mmol) in anhydrous DMSO (8 mL) was stirred at 93° C. for 9 h. After cooling, the reaction mixture was poured into ice-water and then extracted with CH$_2$Cl$_2$-MeOH. The organic layer was washed with water and brine, and dried over anhyd Na$_2$SO$_4$ followed by the removal of solvent. The crude product was purified by column chromatography (EtOAc) to yield (3S)-8-amino-9-fluoro-2,3-dihydro-3-methyl-7-oxo-10-[cis-3-(3-pyridyl)cyclohexylamino]-7H-pyrido[1,2,3-de][1,4]benzoxazine-6-carbonitrile (96.0 mg, 13%) as a yellow powder.

$^1$H-NMR (DMSO-d$_6$, 400 MHz) δ 1.44-1.68 (8H, m), 1.81 (2H, dd, J=37.2, 11.2 Hz), 1.95-2.08 (2H, m), 2.69 (1H, t, J=11.2 Hz), 3.75-3.88 (1H, m), 4.04 (1H, d, J=10.9 Hz), 4.32 (1H, d, J=11.5 Hz), 4.38-4.50 (1H, m), 4.95 (1H, d, J=9.7 Hz), 6.94 (2H, brs), 7.30 (1H, dd, J=7.3, 4.8 Hz), 7.60-7.68 (1H, m), 8.39 (1H, d, J=4.2 Hz), 8.45 (2H, s).

ESIMS (+): 434.2 [M+H]$^+$.
HRESIMS (+): 434.19890 (Calcd for C$_{24}$H$_{25}$FN$_5$O$_2$, 434.19923).

Example 11

Gs Activation

HepG2 cells were obtained from the Japanese Collection of Research Bioresources and were grown in standard culture medium, a low-glucose Dulbecco's modified Eagle's medium (DMEM) containing 10% fetal calf serum supplemented with 100 U/mL penicillin and 100 µg/mL streptomycin, in a humidified and 5% CO$_2$ atmosphere kept at 37° C. The HepG2 cells were harvested with 0.25% trypsin solution containing 1 mM EDTA, and were seeded on 12 well plates at 1×10$^5$ cells per well. Following a culture for 3 days, the cells were washed once with phosphate buffered saline (PBS), and were incubated with serum-free low-glucose DMEM supplemented with 100 U/mL penicillin and 100 µg/mL streptomycin. Following a culture for 3 hrs, GSK-3 inhibitor at various concentration and 2.5 µCi/mL D-[2-$^3$H]glucose (New England Nuclear, Boston, Mass., USA) were added to the serum-free low-glucose DMEM. A vehicle control of DMSO (0.3%, final concentration) was also used. Total volume per well of the reaction medium was 1.0 mL of serum-free low-glucose DMEM. After incubation at 37° C. for 3 hrs, medium was aspirated and cells were washed twice with PBS, and were added 0.25 mL of 1 N KOH containing 0.4 mg/mL carrier glycogen. After incubation at 37° C. for 30 min, 0.25 mL of 48.8% (w/v) KOH was added to well for cell lysis. After incubation at 95° C. for 30 min, 1.5 mL of 95% (v/v) ethanol was added to the cell lysate. Total glycogen was precipitated overnight at −20° C. Glycogen precipitates were recovered by centrifugation at 19,000×g for 30 min at 4° C. Precipitates were washed once with 1 mL of 70% (v/v) ethanol, and were re-suspended in 0.5 mL water. [$^3$H]Glucose incorporation into glycogen was assessed using a liquid scintillation counter (Packard Instrument Co., Meriden, Conn., USA).

EC$_{50}$ for glycogen synthesis of the compounds of Example 7, 9, 10 was 0.3 µM or lower.

Example 12

Animal Study: Glucose Tolerance Study

Male Crlj:CD1 (ICR) mice were obtained from Charles River Laboratories Japan (Yokohama, Japan). All mice were given a standard diet (Clea Japan, Tokyo, Japan) and tap water ad libitum. All institutional guidelines for animal care and use were applied in this study. Test compounds were suspended in 0.3% carbozymethyl-cellulose sodium salt (CMC-Na; Sigma, St. Louis, Mo.). After fasting for 15-17 hours, the test compound (3, 10, 30, 100 or 300 mg/kg) or vehicle (0.3% CMC-Na) was orally administered to 7-week-old ICR mice. Glucose solution (5 g/kg) was orally administered at 30 minutes after test compound treatment. Blood samples were collected from tail vein using capillary tubes containing EDTA-2K before test compound treatment, and at 0, 0.5, 1, and 2 hours after glucose load. The blood samples were centrifuged at 2,500×g for 5 minutes and separated plasma was kept on ice and analyze in the same day. Plasma glucose levels were determined using the glucose CII-test (Wako Pure Chemical Industries, Osaka, Japan). The sum of plasma glucose levels at 0.5 and 1 hr after glucose load was compared to that of vehicle treatment, and results were presented as percent decrease.

The compound of Example 2 (10 mg/kg) showed 22% decrease.

Since modifications will be apparent to those of skill in the art, it is intended that the claimed subject matter be limited only by the scope of the appended claims.

What is claimed is:

1. A compound of Formula (I):

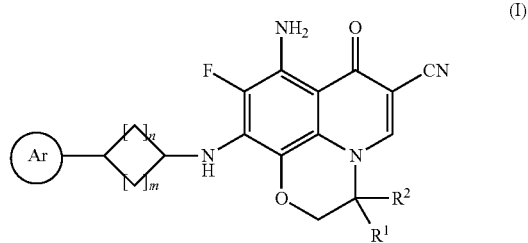

or a pharmaceutically acceptable salt thereof, wherein

R$^1$ is lower alkyl;

R$^2$ is hydrogen or lower alkyl;

m is 1, 2 or 3; and n is 1 or 2;

Ar is aryl or heteroaryl which is optionally substituted with one to three substituents, each independently selected from Q groups;

wherein Q is halo, hydroxy, cyano, nitro, oxo, thioxo, hydroxycarbonyl, alkyl, haloalkyl, alkenyl, alkynyl, cycloalkyl, heterocyclyl, aryl, heteroaryl, aralkyl, heteroaralkyl, alkoxy, haloalkoxy, cycloalkoxy, heterocyclyloxy, aryloxy, heteroaryloxy, aralkyloxy, heretoaralkyloxy, alkylcarbonyl, arylcarbonyl, heteroarylcarbonyl, alkoxycarbonyl, aryloxycarbonyl, aralkyloxycarbonyl, unsubstituted or substituted aminocarbonyl, alkylcarbonyloxy, arylcarbonyloxy, aralkylcarbonyloxy, alkoxycarbonyloxy, aryloxycarbonyloxy, aralkyloxycarbonyloxy, unsubstituted or substituted aminocarbonyloxy, unsubstituted or substituted amino, alkylthio, cycloalkylthio, arylthio, heteroarylthio, aralkylthio, heteroaralkylthio, alkylsulfinyl, cycloalkylsulfinyl, arylsulfinyl, heteroarylsulfinyl, aralkylsulfinyl, heteroaralkylsulfinyl, alkylsulfonyl, cycloalkylsulfonyl, arylsulfonyl, heteroarylsulfonyl, aralkylsulfonyl, heteroaralkylsulfonyl, alkoxysulfonyl, aryloxysulfonyl, unsubstituted or substituted aminosulfonyl, or hydroxysulfonyl.

2. The compound of claim 1, wherein R$^2$ is hydrogen.

3. The compound of claim 1, wherein Ar is heteroaryl which is optionally substituted with one to three substituents, each independently selected from Q groups.

4. The compound of claim 1, wherein m+n is 3 or 4.

5. The compound of claim 1 having Formula (Ia):

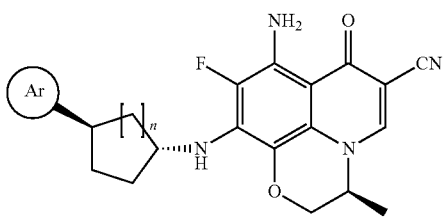

(Ia)

or a pharmaceutically acceptable salt thereof, wherein n is 1 or 2; and

Ar is aryl or heteroaryl which is optionally substituted with one to three substituents, each independently selected from Q groups;

wherein Q is halo, hydroxy, cyano, nitro, oxo, thioxo, hydroxycarbonyl, alkyl, haloalkyl, alkenyl, alkynyl, cycloalkyl, heterocyclyl, aryl, heteroaryl, aralkyl, heteroaralkyl, alkoxy, haloalkoxy, cycloalkoxy, heterocyclyloxy, aryloxy, heteroaryloxy, aralkyloxy, heretoaralkyloxy, alkylcarbonyl, arylcarbonyl, heteroarylcarbonyl, alkoxycarbonyl, aryloxycarbonyl, aralkyloxycarbonyl, unsubstituted or substituted aminocarbonyl, alkylcarbonyloxy, arylcarbonyloxy, aralkylcarbonyloxy, alkoxycarbonyloxy, aryloxycarbonyloxy, aralkyloxycarbonyloxy, unsubstituted or substituted aminocarbonyloxy, unsubstituted or substituted amino, alkylthio, cycloalkylthio, arylthio, heteroarylthio, aralkylthio, heteroaralkylthio, alkylsulfinyl, cycloalkylsulfinyl, arylsulfinyl, heteroarylsulfinyl, aralkylsulfinyl, heteroaralkylsulfinyl, alkylsulfonyl, cycloalkylsulfonyl, arylsulfonyl, heteroarylsulfonyl, aralkylsulfonyl, heteroaralkylsulfonyl, alkoxysulfonyl, aryloxysulfonyl, unsubstituted or substituted aminosulfonyl, or hydroxysulfonyl.

6. The compound of claim 5, wherein Ar is heteroaryl which is optionally substituted with one to three substituents, each independently selected from Q groups.

7. The compound of claim 6, wherein Ar is pyridyl, pyramidyl, pyrazolyl or imidazolyl, which is optionally substituted with one to three substituents, each independently selected from Q groups.

8. The compound of claim 1 selected from:

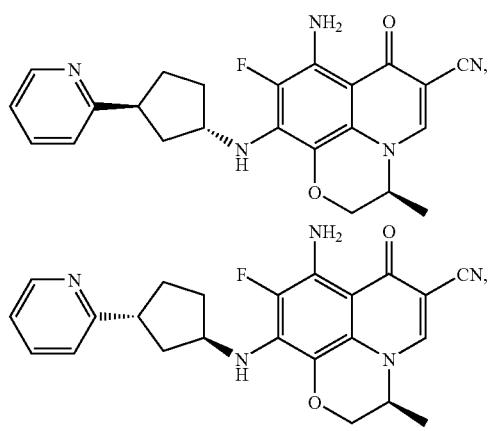

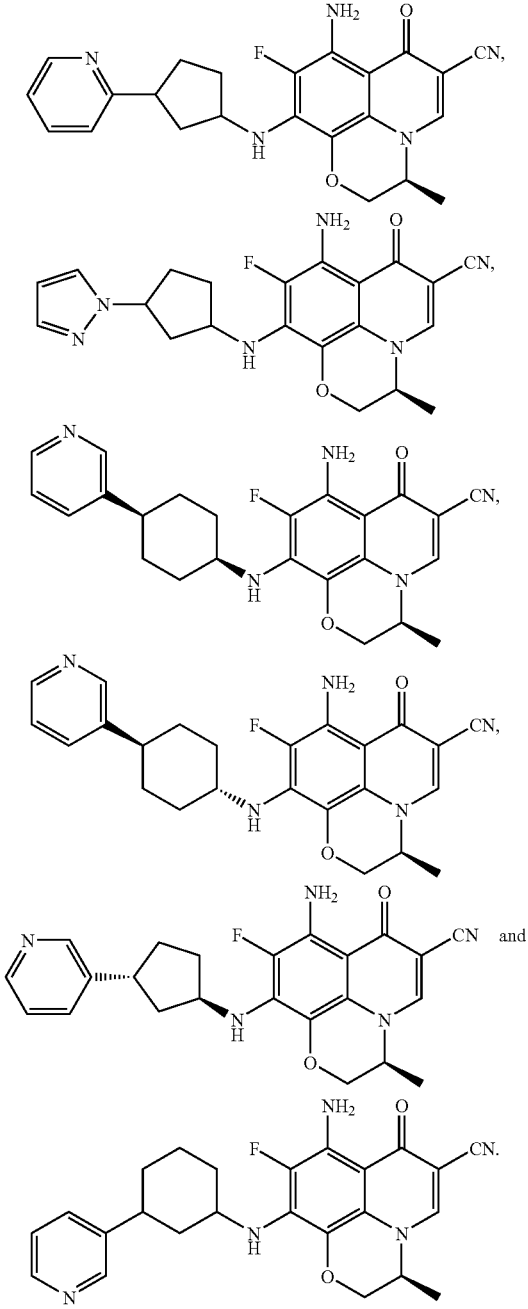

9. A pharmaceutical composition comprising a compound of claim 1 and a pharmaceutically acceptable carrier.

10. A method for treating, or ameliorating a GSK-3 mediated disease comprising administering a compound of claim 1, wherein the disease is selected from Parkinson's disease, progressive supranuclear palsy, subacute sclerosing panencephalitic parkinsonism, postencephalitic parkinsonism, pugilistic encephalitis, guam parkinsonism-dementia complex, Pick's disease, corticobasal degeneration, frontotemporal dementia, Huntington's Disease, AIDS associated dementia, amyotrophic lateral sclerosis, multiple sclerosis, neurotraumatic diseases, depression, a bipolar mood disorder, rheumatoid arthritis, inflammatory bowel disease, ulcerative colitis, Crohn's disease, sepsis, pancreatic cancer, ovarian cancer or osteoporosis.

* * * * *